United States Patent
Pompejus

(10) Patent No.: US 9,249,448 B2
(45) Date of Patent: Feb. 2, 2016

(54) MALODOUR STANDARDS AND INHIBITORS

(75) Inventor: Markus Pompejus, White Plains, NY (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/994,289

(22) PCT Filed: Dec. 19, 2011

(86) PCT No.: PCT/EP2011/073275
§ 371 (c)(1),
(2), (4) Date: Jun. 14, 2013

(87) PCT Pub. No.: WO2012/080516
PCT Pub. Date: Jun. 21, 2012

(65) Prior Publication Data
US 2013/0315851 A1    Nov. 28, 2013

Related U.S. Application Data

(60) Provisional application No. 61/424,114, filed on Dec. 17, 2010.

(30) Foreign Application Priority Data

Dec. 17, 2010  (EP) .................................. 10195789

(51) Int. Cl.
*C12Q 1/25* (2006.01)
*C12N 9/84* (2006.01)
*A61K 8/36* (2006.01)
*A61Q 15/00* (2006.01)

(52) U.S. Cl.
CPC ... *C12Q 1/25* (2013.01); *A61K 8/36* (2013.01); *A61Q 15/00* (2013.01); *C12N 9/84* (2013.01)

(58) Field of Classification Search
None
See application file for complete search history.

(56) References Cited

U.S. PATENT DOCUMENTS

2010/0222429 A1*  9/2010  Natsch et al. ............... 514/562

FOREIGN PATENT DOCUMENTS

WO   WO 02/092024   11/2002

OTHER PUBLICATIONS

Uniprot Accession No. Q2HPP6_BACIU, published Mar. 21, 2006.*
GenBank Accession No. EFG93792.1, published May 17, 2010.*
GenBank Accession No. CAJ77223.1, published Feb. 22, 2006.*
Gaurschi et al., "Biochemistry of human axilla malodor and chemistry of deodorant ingredients", Chimia, vol. 61, pp. 27-32, 2007.*
Ara et al., "Foot odor due to microbial metabolism and its control", Canadian Journal of Microbiology, vol. 52, pp. 357-364, 2006.*

(Continued)

*Primary Examiner* — Robert Mondesi
*Assistant Examiner* — Richard Ekstrom
(74) *Attorney, Agent, or Firm* — Servilla Whitney LLC

(57) ABSTRACT

The invention pertains to the field of reaction systems generating malodor, particularly from constituents of human sweat. Specifically, the invention pertains to proteins for generating malodors, substrates for generating such malodor, inhibitors of such malodor generation and test and screening systems for measuring their malodor inhibition efficacy and finding substances previously not known to inhibit malodor generation. Thus, the invention also pertains to the field of deodorants.

13 Claims, 16 Drawing Sheets

```
SEQ ID NO 1:

MCTSLTLETA   DRKHVLARTM   DFAFQLGTEV   ILYPRRYSWN   SEADGRAHQT
QYAFIGMGRK   LGNILFADAF   NESGLSCAAL   YFPGYAEYEK   MIREDTVHIV
PHEFVTWVLS   VCQSLEDVKE   KIRSLTIVEK   KLDLLDTVLP   LHWILSDRTG
RNLTIEPRAD   GLKVYDNQPG   VMTNSPDFIW   HVTNLQQYTG   IRPKQLESKE
MGGLALSAFG   QGLGTVGLSG   DYTPPSRFVR   AVYLKEHLEP   AADETKGVTA
AFQILANMTI   PKGAVITEED   EIHYTQYTSV   MCNETGNYYF   HHYDNRQIQK
VNLFHEDLDC   LEPKVFSAKA   EESIHELN
```

(56) References Cited

OTHER PUBLICATIONS

Natsch et al., "A broad diversity of volatile carboxylic acids, released by a bacterial aminoacylase from axilla secretions, as candidate molecules for the determination of human-body odor type", Chemistry and Biodiversity, vol. 3, pp. 1-20, 2006.*
Natsch et al., "Isolation of a bacterial enzyme releasing axillary malodor and its use as a screening target for novel deodorant formulations", International Journal of Cosmetic Science, vol. 27, pp. 115-122, 2005.*
Natsch et al., "Identification of odoriferous sulfanylalkanols in human axilla secretions and their formation through cleavage of cysteine precursors by a C-S lyase isolated from axilla bacteria", Chemistry and Biodiversity, vol. 1, pp. 1058-1072, 2004.*
Natsch et al., "A specific bacterial aminoacylase cleaves odorant precursors secreted in the human axilla", Journal of Biological Chemistry, vol. 278, No. 8, pp. 5718-5727, 2003.*
*Bacillus subtilis* hypothetical protein homologous to pencillin acylase, *EMBL (Online) Database XP-002676438* 2003, 2 pgs.
*Bacillus subtilis* yxel gene for penicillin V acylase, *EMBL (Online) Database XP002676440* 2006, 2 pgs.
International Search Report and Written Opinion of PCT/EP2011/073275, mailed on Oct. 26, 2012, 19 pgs.
SubName: Full=Penicillin V acylase; EC=3.5.1.11, *UniProt (Online) Database XP-002676444* 2006, 1 pg.
SubName: Full=Putative hydrolase, *UniProt (Online) Database XP-002676441* 2010, 1 pg.
SubName: Full=Putative hydrolase, *UniProt (Online) Database XP-002676442* 2010, 1 pg.
SubName: Full=Putative uncharacterized protein yxel, *UniProt (Online) Database XP-002676443* 2010, 1 pg.
Needleman, Saul B. et al., "A General Method Applicable to the Search for Similarities in the Amino Acid Sequence of Two Proteins", *J. Mol. Biol.*, vol. 48 1970, pp. 443-453.
Rathinaswamy, Priya et al., "Cloning, purification, crystallization and preliminary structural studies of penicillin V acylase from *Bacillus subtilis*", *Acta. Cryst.* 2005 F61 pp. 680-683.
Coding: BAA08325.1 *Bacillus subtilis* hypothetical protein, *ENA European Nucleotide Archive*, http://www.ebi.ac.uk/ena/data/view/BAA08325 accessed from the Internet Dec. 4, 2014, 2 pages.
D4G3U7—D4G3U7 BACNB—Uncharacterized protein, *UniProt*, http://www.uniprot.org/uniprot/D4G3U7 accessed from the Internet Dec. 4, 2014, 5 pages.
D5MWB7—D5MWB7 BACPN—Putative hydrolase, *UniProt*, http://www.uniprot.org/uniprot/D5MWB7 accessed from the Internet Dec. 4, 2014, 4 pages.
E0TYE2—E0TYE2_—Putative hydrolase, *UniProt*, http://www.uniprot.org/uniprot/E0TYE2 accessed from the Internet Dec. 4, 2014, 5 pages.
Q2HPP6—Q2HPP6_BACIU—Penicillin V acylase, *UniProt*, http://www.uniprot.org/uniprot/Q2HPP6 accessed from the Internet Dec. 4, 2014, 5 pages.
Kuhn, Fabian, et al., Body odour of monozygotic human twins: a common pattern of odorant carboxylic acids released by a bacterial aminoacylase from axilla secretions contributing to an inherited body odour type, *J. R. Soc. Interface* vol. 6 2009, 377-392.
Rathinaswamy, Priya, et al., Purification and characterization of Yxel, a penicillin acylase from *Bacillus subtilis*, *International Journal of Biological Macromolecules* vol. 50 2012, 25-30.

* cited by examiner

SEQ ID NO 1:

```
MCTSLTLETA  DRKHVLARTM  DFAFQLGTEV  ILYPRRYSWN  SEADGRAHQT
QYAFIGMGRK  LGNILFADAF  NESGLSCAAL  YFPGYAEYEK  MIREDTVHIV
PHEFVTWVLS  VCQSLEDVKE  KIRSLTIVEK  KLDLLDTVLP  LHWILSDRTG
RNLTIEPRAD  GLKVYDNQPG  VMTNSPDFIW  HVTNLQQYTG  IRPKQLESKE
MGGLALSAFG  QGLGTVGLSG  DYTPPSRFVR  AVYLKEHLEP  AADETKGVTA
AFQILANMTI  PKGAVITEED  EIHYTQYTSV  MCNETGNYYF  HHYDNRQIQK
VNLFHEDLDC  LEPKVFSAKA  EESIHELN
```

Fig.1

SEQ ID NO 2:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 2

SEQ ID NO 34:

SEQ ID NO 35:

SEQ ID NO 5:

| | | | | |
|---|---|---|---|---|
| MCTSLTLETA | DRKHLLARTM | DFAFQLGTEV | ILYPRRYNWM | SEADGKAHQT |
| QYAFIGMGRK | LGNILFADGI | NENGLSCAAL | YFPGYAEYEK | TIQEATVHIA |
| PHEFVTWALS | SCKSLEDVKE | KMRSLTIVEK | KLDLLDTVLP | LHWILSDRTG |
| RSLTIEPRAE | GLKVYDNQPG | VMTNSPDFIW | HVTNLQQYTG | IRPKQLESKE |
| MGGLALSAFG | QGLGTIGLPG | DYTPPSRFVR | AVYLKEHLEP | AADETKGVTA |
| AFQLLANMTV | PKGAVITEKD | EIHYTQYTSV | MCNDTGNYYF | HLYDNRQIQK |
| VNLFHEDLDR | LEPKVFSAKA | EESIHELN | | |

Fig. 5

SEQ ID NO 6:

| | | | | |
|---|---|---|---|---|
| MCTSLTLETA | DRNHVLARTM | DFAFQLGTEV | ILYPRRYNWM | SEADGKAHQT |
| QYAFIGMGRK | LGNILFADGI | NENGLSCAAL | YFPGYAEYEK | TIQEATVHIA |
| PHEFVTWALS | SCKSLEDVKE | KMRSLTIVEK | KLDLLDTVLP | LHWILSDRTG |
| RSLTIEPRAE | GLKVYDNQPG | VMTNSPDFIW | HVTNLQQYTG | IRPKQLESKE |
| MGGLALSAFG | QGLGTIGLPG | DYTPPSRFVR | AVYLKEHLEP | AADETKGVTA |
| AFQLLANMTV | PKGAVITEKD | EIHYTQYTSV | MCNDTGNYYF | HLYDNRQIQK |
| VNLFHEDLDR | LEPKVFSAKA | EESIHELN | | |

Fig. 6

SEQ ID NO 7:

| | | | | |
|---|---|---|---|---|
| MCTSLTLETA | DRNHLLARTM | DFAFQLGTEV | ILYPRRYSWM | SEADGKAHQT |
| QYAFIGMGRK | LGNILFADGI | NENGLSCAAL | YFPGYAEYEK | TIQEATVHIA |
| PHEFVTWALS | SCKSLEDVKE | KMRSLTIVEK | KLDLLDTVLP | LHWILSDRTG |
| RSLTIEPRAE | GLKVYDNQPG | VMTNSPDFIW | HVTNLQQYTG | IRPKQLESKE |
| MGGLALSAFG | QGLGTIGLPG | DYTPPSRFVR | AVYLKEHLEP | AADETKGVTA |
| AFQLLANMTV | PKGAVITEKD | EIHYTQYTSV | MCNDTGNYYF | HLYDNRQIQK |
| VNLFHEDLDR | LEPKVFSAKA | EESIHELN | | |

Fig. 7

SEQ ID NO 8:

```
MCTSLTLETA  DRNHLLARTM  DFAFQLGTEV  ILYPRRYNWN  SEADGKAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 8

SEQ ID NO 9:

```
MCTSLTLETA  DRNHLLARTM  DFAFQLGTEV  ILYPRRYNWM  SEADGRAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 9

SEQ ID NO 10:

```
MCTSLTLETA  DRNHLLARTM  DFAFQLGTEV  ILYPRRYNWM  SEADGKAHQT
QYAFIGMGRK  LGNILFADAI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 10

SEQ ID NO 11:

MCTSLTLETA DRNHLLARTM DFAFQLGTEV ILYPRRYNWM SEADGKAHQT
QYAFIGMGRK LGNILFADGF NENGLSCAAL YFPGYAEYEK TIQEATVHIA
PHEFVTWALS SCKSLEDVKE KMRSLTIVEK KLDLLDTVLP LHWILSDRTG
RSLTIEPRAE GLKVYDNQPG VMTNSPDFIW HVTNLQQYTG IRPKQLESKE
MGGLALSAFG QGLGTIGLPG DYTPPSRFVR AVYLKEHLEP AADETKGVTA
AFQLLANMTV PKGAVITEKD EIHYTQYTSV MCNDTGNYYF HLYDNRQIQK
VNLFHEDLDR LEPKVFSAKA EESIHELN

Fig. 11

SEQ ID NO 12:

MCTSLTLETA DRNHLLARTM DFAFQLGTEV ILYPRRYNWM SEADGKAHQT
QYAFIGMGRK LGNILFADGI NESGLSCAAL YFPGYAEYEK TIQEATVHIA
PHEFVTWALS SCKSLEDVKE KMRSLTIVEK KLDLLDTVLP LHWILSDRTG
RSLTIEPRAE GLKVYDNQPG VMTNSPDFIW HVTNLQQYTG IRPKQLESKE
MGGLALSAFG QGLGTIGLPG DYTPPSRFVR AVYLKEHLEP AADETKGVTA
AFQLLANMTV PKGAVITEKD EIHYTQYTSV MCNDTGNYYF HLYDNRQIQK
VNLFHEDLDR LEPKVFSAKA EESIHELN

Fig. 12

SEQ ID NO 13:

MCTSLTLETA DRNHLLARTM DFAFQLGTEV ILYPRRYNWM SEADGKAHQT
QYAFIGMGRK LGNILFADGI NENGLSCAAL YFPGYAEYEK MIQEATVHIA
PHEFVTWALS SCKSLEDVKE KMRSLTIVEK KLDLLDTVLP LHWILSDRTG
RSLTIEPRAE GLKVYDNQPG VMTNSPDFIW HVTNLQQYTG IRPKQLESKE
MGGLALSAFG QGLGTIGLPG DYTPPSRFVR AVYLKEHLEP AADETKGVTA
AFQLLANMTV PKGAVITEKD EIHYTQYTSV MCNDTGNYYF HLYDNRQIQK
VNLFHEDLDR LEPKVFSAKA EESIHELN

Fig. 13

SEQ ID NO 14:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIREATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 14

SEQ ID NO 15:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEDTVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 15

SEQ ID NO 16:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIV
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 16

SEQ ID NO 17:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWVLS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 17

SEQ ID NO 18:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  VCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 18

SEQ ID NO 19:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCQSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 19

SEQ ID NO 20:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCKSLEDVKE  KIRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 20

SEQ ID NO 21:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RNLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 21

SEQ ID NO 22:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAD  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDR  LEPKVFSAKA  EESIHELN
```

Fig. 22

SEQ ID NO 23:

| MCTSLTLETA | DRNHLLARTM | DFAFQLGTEV | ILYPRRYNWM | SEADGKAHQT |
| QYAFIGMGRK | LGNILFADGI | NENGLSCAAL | YFPGYAEYEK | TIQEATVHIA |
| PHEFVTWALS | SCKSLEDVKE | KMRSLTIVEK | KLDLLDTVLP | LHWILSDRTG |
| RSLTIEPRAE | GLKVYDNQPG | VMTNSPDFIW | HVTNLQQYTG | IRPKQLESKE |
| MGGLALSAFG | QGLGTVGLPG | DYTPPSRFVR | AVYLKEHLEP | AADETKGVTA |
| AFQLLANMTV | PKGAVITEKD | EIHYTQYTSV | MCNDTGNYYF | HLYDNRQIQK |
| VNLFHEDLDR | LEPKVFSAKA | EESIHELN | | |

Fig. 23

SEQ ID NO 24:

| MCTSLTLETA | DRNHLLARTM | DFAFQLGTEV | ILYPRRYNWM | SEADGKAHQT |
| QYAFIGMGRK | LGNILFADGI | NENGLSCAAL | YFPGYAEYEK | TIQEATVHIA |
| PHEFVTWALS | SCKSLEDVKE | KMRSLTIVEK | KLDLLDTVLP | LHWILSDRTG |
| RSLTIEPRAE | GLKVYDNQPG | VMTNSPDFIW | HVTNLQQYTG | IRPKQLESKE |
| MGGLALSAFG | QGLGTIGLSG | DYTPPSRFVR | AVYLKEHLEP | AADETKGVTA |
| AFQLLANMTV | PKGAVITEKD | EIHYTQYTSV | MCNDTGNYYF | HLYDNRQIQK |
| VNLFHEDLDR | LEPKVFSAKA | EESIHELN | | |

Fig. 24

SEQ ID NO 25:

| MCTSLTLETA | DRNHLLARTM | DFAFQLGTEV | ILYPRRYNWM | SEADGKAHQT |
| QYAFIGMGRK | LGNILFADGI | NENGLSCAAL | YFPGYAEYEK | TIQEATVHIA |
| PHEFVTWALS | SCKSLEDVKE | KMRSLTIVEK | KLDLLDTVLP | LHWILSDRTG |
| RSLTIEPRAE | GLKVYDNQPG | VMTNSPDFIW | HVTNLQQYTG | IRPKQLESKE |
| MGGLALSAFG | QGLGTIGLPG | DYTPPSRFVR | AVYLKEHLEP | AADETKGVTA |
| AFQILANMTV | PKGAVITEKD | EIHYTQYTSV | MCNDTGNYYF | HLYDNRQIQK |
| VNLFHEDLDR | LEPKVFSAKA | EESIHELN | | |

Fig. 25

SEQ ID NO 26:

MCTSLTLETA DRNHLLARTM DFAFQLGTEV ILYPRRYNWM SEADGKAHQT
QYAFIGMGRK LGNILFADGI NENGLSCAAL YFPGYAEYEK TIQEATVHIA
PHEFVTWALS SCKSLEDVKE KMRSLTIVEK KLDLLDTVLP LHWILSDRTG
RSLTIEPRAE GLKVYDNQPG VMTNSPDFIW HVTNLQQYTG IRPKQLESKE
MGGLALSAFG QGLGTIGLPG DYTPPSRFVR AVYLKEHLEP AADETKGVTA
AFQLLANMTI PKGAVITEKD EIHYTQYTSV MCNDTGNYYF HLYDNRQIQK
VNLFHEDLDR LEPKVFSAKA EESIHELN

Fig. 26

SEQ ID NO 27:

MCTSLTLETA DRNHLLARTM DFAFQLGTEV ILYPRRYNWM SEADGKAHQT
QYAFIGMGRK LGNILFADGI NENGLSCAAL YFPGYAEYEK TIQEATVHIA
PHEFVTWALS SCKSLEDVKE KMRSLTIVEK KLDLLDTVLP LHWILSDRTG
RSLTIEPRAE GLKVYDNQPG VMTNSPDFIW HVTNLQQYTG IRPKQLESKE
MGGLALSAFG QGLGTIGLPG DYTPPSRFVR AVYLKEHLEP AADETKGVTA
AFQLLANMTV PKGAVITEED EIHYTQYTSV MCNDTGNYYF HLYDNRQIQK
VNLFHEDLDR LEPKVFSAKA EESIHELN

Fig. 27

SEQ ID NO 28:

MCTSLTLETA DRNHLLARTM DFAFQLGTEV ILYPRRYNWM SEADGKAHQT
QYAFIGMGRK LGNILFADGI NENGLSCAAL YFPGYAEYEK TIQEATVHIA
PHEFVTWALS SCKSLEDVKE KMRSLTIVEK KLDLLDTVLP LHWILSDRTG
RSLTIEPRAE GLKVYDNQPG VMTNSPDFIW HVTNLQQYTG IRPKQLESKE
MGGLALSAFG QGLGTIGLPG DYTPPSRFVR AVYLKEHLEP AADETKGVTA
AFQLLANMTV PKGAVITEKD EIHYTQYTSV MCNETGNYYF HLYDNRQIQK
VNLFHEDLDR LEPKVFSAKA EESIHELN

Fig. 28

SEQ ID NO 29:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HHYDNRQIQK
VNLFHEDLDR  LEPKVFSAKA  EESIHELN
```

Fig. 29

SEQ ID NO 30:

```
MCTSLTLETA  DRNHLLARTM  DFAFQLGTEV  ILYPRRYNWM  SEADGKAHQT
QYAFIGMGRK  LGNILFADGI  NENGLSCAAL  YFPGYAEYEK  TIQEATVHIA
PHEFVTWALS  SCKSLEDVKE  KMRSLTIVEK  KLDLLDTVLP  LHWILSDRTG
RSLTIEPRAE  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQLLANMTV  PKGAVITEKD  EIHYTQYTSV  MCNDTGNYYF  HLYDNRQIQK
VNLFHEDLDC  LEPKVFSAKA  EESIHELN
```

Fig. 30

SEQ ID NO 31:

```
MCTSLTLETA  DRNHVLARTM  DFAFQLGTEV  ILYPRRYSWM  SEADGRAHQT
QYAFIGMGRK  LGNILFADGI  NESGLSCAAL  YFPGYAEYEK  TIREATVHIA
PHEFVTWALS  SCQSLEDVKE  KIRSLTIVEK  KLDLLDTVLP  LHWILSDRTG
RNLTIEPRAD  GLKVYDNQPG  VMTNSPDFIW  HVTNLQQYTG  IRPKQLESKE
MGGLALSAFG  QGLGTIGLPG  DYTPPSRFVR  AVYLKEHLEP  AADETKGVTA
AFQILANMTI  PKGAVITEED  EIHYTQYTSV  MCNETGNYYF  HLYDNRQIQK
VNLFHEDLDR  LEPKVFSAKA  EESIHELN
```

Fig. 31

SEQ ID NO 32:

```
ATGTGCACATCTCTTACACTTGAAACAGCTGATCGTAACCATCTTCTTGC    50
TCGTACAATGGATTTCGCTTTCCAACTTGGCACAGAAGTTATCCTTTACC   100
CTCGTCGTTACAACTGGATGTCTGAAGCTGATGGCAAAGCTCATCAAACA   150
CAATACGCTTTCATCGGCATGGGCCGTAAACTTGGCAACATCCTTTTCGC   200
TGATGGCATCAACGAAAACGGCCTTTCTTGCGCTGCTCTTTACTTCCCTG   250
GCTACGCTGAATACGAAAAACAATCCAAGAAGCTACAGTTCATATCGCT    300
CCTCATGAATTCGTTACATGGCTCTTTCTTCTTGCAAATCTCTTGAAGA    350
TGTTAAAGAAAAAATGCGTTCTCTTACAATCGTTGAAAAAAAACTTGATC   400
TTCTTGATACAGTTCTTCCTCTTCATTGGATCCTTTCTGATCGTACAGGC   450
CGTTCTCTTACAATCGAACCTCGTGCTGAAGGCCTTAAAGTTTACGATAA   500
CCAACCTGGCGTTATGACAAACTCTCCTGATTTCATCTGGCATGTTACAA   550
ACCTTCAACAATACACAGGCATCCGTCCTAAACAACTTGAATCTAAAGAA   600
ATGGGCGGCCTTGCTCTTTCTGCTTTCGGCCAAGGCCTTGGCACAATCGG   650
CCTTCCTGGCGATTACACACCTCCTTCTCGTTTCGTTCGTGCTGTTTACC   700
TTAAAGAACATCTTGAACCTGCTGCTGATGAAACAAAAGGCGTTACAGCT   750
GCTTTCCAACTTCTTGCTAACATGACAGTTCCTAAAGGCGCTGTTATCAC   800
AGAAAAAGATGAAATCCATTACACACAATACACATCTGTTATGTGCAACG   850
ATACAGGCAACTACTACTTCCATCTTTACGATAACCGTCAAATCCAAAAA   900
GTTAACCTTTTCCATGAAGATCTTGATCGTCTTGAACCTAAAGTTTTCTC   950
TGCTAAAGCTGAAGAATCTATCCATGAACTTAAC
```

Fig. 32

SEQ ID NO 33:

```
ATGTGCACCTCTCTGACCCTGGAAACCGCTGACCGTAACCACCTGCTGGC    50
TCGTACCATGGACTTCGCTTTCCAGCTGGGTACCGAAGTTATCCTGTACC   100
CGCGTCGTTACAACTGGATGTCTGAAGCTGACGGTAAAGCTCACCAGACC   150
CAGTACGCTTTCATCGGTATGGGTCGTAAACTGGGTAACATCCTGTTCGC   200
TGACGGTATCAACGAAAACGGTCTGTCTTGCGCTGCTCTGTACTTCCCGG   250
GTTACGCTGAATACGAAAAAACCATCCAGGAAGCTACCGTTCACATCGCT   300
CCGCACGAATTCGTTACCTGGGCTCTGTCTTCTTGCAAATCTCTGGAAGA   350
CGTTAAAGAAAAATGCGTTCTCTGACCATCGTTGAAAAAAAACTGGACC   400
TGCTGGACACCGTTCTGCCGCTGCACTGGATCCTGTCTGACCGTACCGGT   450
CGTTCTCTGACCATCGAACCGCGTGCTGAAGGTCTGAAAGTTTACGACAA   500
CCAGCCGGGTGTTATGACCAACTCTCCGGACTTCATCTGGCACGTTACCA   550
ACCTGCAGCAGTACACCGGTATCCGTCCGAAACAGCTGGAATCTAAAGAA   600
ATGGGTGGTCTGGCTCTGTCTGCTTTCGGTCAGGGTCTGGGTACCATCGG   650
TCTGCCGGGTGACTACACCCCGCCGTCTCGTTTCGTTCGTGCTGTTTACC   700
TGAAAGAACACCTGGAACCGGCTGCTGACGAAACCAAAGGTGTTACCGCT   750
GCTTTCCAGCTGCTGGCTAACATGACCGTTCCGAAAGGTGCTGTTATCAC   800
CGAAAAAGACGAAATCCACTACACCCAGTACACCTCTGTTATGTGCAACG   850
ACACCGGTAACTACTACTTCCACCTGTACGACAACCGTCAGATCCAGAAA   900
GTTAACCTGTTCCACGAAGACCTGGACCGTCTGGAACCGAAAGTTTTCTC   950
TGCTAAAGCTGAAGAATCTATCCACGAACTGAAC
```

Fig. 33

SEQUENCE LISTING

<160> NUMBER OF SEQ ID NOS: 37

<210> SEQ ID NO 1
<211> LENGTH: 328
<212> TYPE: PRT

```
<213> ORGANISM: Bacillus subtilis
<220> FEATURE:
<221> NAME/KEY: Source
<222> LOCATION: (1)..(328)

<400> SEQUENCE: 1
```

| | | | | | | | | | | | | | | |
|---|---|---|---|---|---|---|---|---|---|---|---|---|---|---|
| Met | Cys | Thr | Ser | Leu | Thr | Leu | Glu | Thr | Ala | Asp | Arg | Lys | His | Val | Leu |
| 1 | | | | 5 | | | | | 10 | | | | | 15 | |

Met Cys Thr Ser Leu Thr Leu Glu Thr Ala Asp Arg Lys His Val Leu
1               5                   10                  15

Ala Arg Thr Met Asp Phe Ala Phe Gln Leu Gly Thr Glu Val Ile Leu
            20                  25                  30

Tyr Pro Arg Arg Tyr Ser Trp Asn Ser Glu Ala Asp Gly Arg Ala His
        35                  40                  45

Gln Thr Gln Tyr Ala Phe Ile Gly Met Gly Arg Lys Leu Gly Asn Ile
50                  55                  60

Leu Phe Ala Asp Ala Phe Asn Glu Ser Gly Leu Ser Cys Ala Ala Leu
65                  70                  75                  80

Tyr Phe Pro Gly Tyr Ala Glu Tyr Glu Lys Met Ile Arg Glu Asp Thr
            85                  90                  95

Val His Ile Val Pro His Glu Phe Val Thr Trp Val Leu Ser Val Cys
                100                 105                 110

Gln Ser Leu Glu Asp Val Lys Glu Lys Ile Arg Ser Leu Thr Ile Val
            115                 120                 125

Glu Lys Lys Leu Asp Leu Leu Asp Thr Val Leu Pro Leu His Trp Ile
130                 135                 140

Leu Ser Asp Arg Thr Gly Arg Asn Leu Thr Ile Glu Pro Arg Ala Asp
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Val Gly Leu Ser Gly Asp Tyr Thr Pro
210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Ile Leu Ala
            245                 250                 255

Asn Met Thr Ile Pro Lys Gly Ala Val Ile Thr Glu Glu Asp Glu Ile
                260                 265                 270

His Tyr Thr Gln Tyr Thr Ser Val Met Cys Asn Glu Thr Gly Asn Tyr
        275                 280                 285

Tyr Phe His His Tyr Asp Asn Arg Gln Ile Gln Lys Val Asn Leu Phe
            290                 295                 300

His Glu Asp Leu Asp Cys Leu Glu Pro Lys Val Phe Ser Ala Lys Ala
305                 310                 315                 320

Glu Glu Ser Ile His Glu Leu Asn
                325

```
<210> SEQ ID NO 2
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat
```

```
<400> SEQUENCE: 2

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 3
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 3

Met Cys Thr Ser Leu Thr Leu Glu Thr Ala Asp Arg Lys His Leu Leu
1               5                   10                  15
```

```
Ala Arg Thr Met Asp Phe Ala Phe Gln Leu Gly Thr Glu Val Ile Leu
             20                  25                  30

Tyr Pro Arg Arg Tyr Asn Trp Met Ser Glu Ala Asp Gly Lys Ala His
             35                  40                  45

Gln Thr Gln Tyr Ala Phe Ile Gly Met Gly Arg Lys Leu Gly Asn Ile
         50                  55                  60

Leu Phe Ala Asp Ala Phe Asn Glu Asn Gly Leu Ser Cys Ala Ala Leu
65                  70                  75                  80

Tyr Phe Pro Gly Tyr Ala Glu Tyr Glu Lys Met Ile Gln Glu Ala Thr
                 85                  90                  95

Val His Ile Ala Pro His Glu Phe Val Thr Trp Ala Leu Ser Ser Cys
            100                 105                 110

Lys Ser Leu Glu Asp Val Lys Glu Lys Ile Arg Ser Leu Thr Ile Val
            115                 120                 125

Glu Lys Lys Leu Asp Leu Leu Asp Thr Val Leu Pro Leu His Trp Ile
            130                 135                 140

Leu Ser Asp Arg Thr Gly Arg Asn Leu Thr Ile Glu Pro Arg Ala Asp
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
            195                 200                 205

Phe Gly Gln Gly Leu Gly Thr Val Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Ile Leu Ala
                245                 250                 255

Asn Met Thr Ile Pro Lys Gly Ala Val Ile Thr Glu Glu Asp Glu Ile
            260                 265                 270

His Tyr Thr Gln Tyr Thr Ser Val Met Cys Asn Asp Thr Gly Asn Tyr
            275                 280                 285

Tyr Phe His His Tyr Asp Asn Arg Gln Ile Gln Lys Val Asn Leu Phe
            290                 295                 300

His Glu Asp Leu Asp Cys Leu Glu Pro Lys Val Phe Ser Ala Lys Ala
305                 310                 315                 320

Glu Glu Ser Ile His Glu Leu Asn
                325
```

<210> SEQ ID NO 4
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 4

```
Met Cys Thr Ser Leu Thr Leu Glu Thr Ala Asp Arg Lys His Leu Leu
1               5                   10                  15

Ala Arg Thr Met Asp Phe Ala Phe Gln Leu Gly Thr Glu Val Ile Leu
             20                  25                  30

Tyr Pro Arg Arg Tyr Asn Trp Met Ser Glu Ala Asp Gly Lys Ala His
             35                  40                  45
```

```
Gln Thr Gln Tyr Ala Phe Ile Gly Met Gly Arg Lys Leu Gly Asn Ile
         50                  55                  60

Leu Phe Ala Asp Ala Phe Asn Glu Asn Gly Leu Ser Cys Ala Ala Leu
 65                  70                  75                  80

Tyr Phe Pro Gly Tyr Ala Glu Tyr Glu Lys Met Ile Gln Glu Ala Thr
                 85                  90                  95

Val His Ile Ala Pro His Glu Phe Val Thr Trp Ala Leu Ser Ser Cys
             100                 105                 110

Lys Ser Leu Glu Asp Val Lys Glu Lys Ile Arg Ser Leu Thr Ile Val
         115                 120                 125

Glu Lys Lys Leu Asp Leu Leu Asp Thr Val Leu Pro Leu His Trp Ile
 130                 135                 140

Leu Ser Asp Arg Thr Gly Arg Asn Leu Thr Ile Glu Pro Arg Ala Asp
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Ile Leu Ala
                245                 250                 255

Asn Met Thr Ile Pro Lys Gly Ala Val Ile Thr Glu Glu Asp Glu Ile
            260                 265                 270

His Tyr Thr Gln Tyr Thr Ser Val Met Cys Asn Asp Thr Gly Asn Tyr
        275                 280                 285

Tyr Phe His His Tyr Asp Asn Arg Gln Ile Gln Lys Val Asn Leu Phe
290                 295                 300

His Glu Asp Leu Asp Cys Leu Glu Pro Lys Val Phe Ser Ala Lys Ala
305                 310                 315                 320

Glu Glu Ser Ile His Glu Leu Asn
                325

<210> SEQ ID NO 5
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 5

Met Cys Thr Ser Leu Thr Leu Glu Thr Ala Asp Arg Lys His Leu Leu
  1               5                  10                  15

Ala Arg Thr Met Asp Phe Ala Phe Gln Leu Gly Thr Glu Val Ile Leu
                 20                  25                  30

Tyr Pro Arg Arg Tyr Asn Trp Met Ser Glu Ala Asp Gly Lys Ala His
             35                  40                  45

Gln Thr Gln Tyr Ala Phe Ile Gly Met Gly Arg Lys Leu Gly Asn Ile
         50                  55                  60

Leu Phe Ala Asp Gly Ile Asn Glu Asn Gly Leu Ser Cys Ala Ala Leu
```

```
                65                  70                  75                  80
Tyr Phe Pro Gly Tyr Ala Glu Tyr Glu Lys Thr Ile Gln Glu Ala Thr
                    85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
                115                 120                 125

Glu Lys Lys Leu Asp Leu Leu Asp Thr Val Leu Pro Leu His Trp Ile
            130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                    165                 170                 175

Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
                195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                    245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
                275                 280                 285

Tyr Phe His Leu Tyr Asp Asn Arg Gln Ile Gln Lys Val Asn Leu Phe
                290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 6
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 6

Met Cys Thr Ser Leu Thr Leu Glu Thr Ala Asp Arg Asn His Val Leu
1               5                   10                  15

Ala Arg Thr Met Asp Phe Ala Phe Gln Leu Gly Thr Glu Val Ile Leu
                20                  25                  30

Tyr Pro Arg Arg Tyr Asn Trp Met Ser Glu Ala Asp Gly Lys Ala His
            35                  40                  45

Gln Thr Gln Tyr Ala Phe Ile Gly Met Gly Arg Lys Leu Gly Asn Ile
        50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                    85                  90                  95
```

```
Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 7
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 7

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Tyr Ser Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125
```

```
Glu Lys Lys Leu Asp Leu Leu Asp Thr Val Leu Pro Leu His Trp Ile
            130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 8
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 8

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Asn Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
```

```
        145                 150                 155                 160
    Gly Leu Lys Val Tyr Asp Asn Gln Pro Gly Val Met Thr Asn Ser Pro
                    165                 170                 175

Asp Phe Ile Trp His Val Thr Asn Leu Gln Gln Tyr Thr Gly Ile Arg
                    180                 185                 190

Pro Lys Gln Leu Glu Ser Lys Glu Met Gly Gly Leu Ala Leu Ser Ala
                    195                 200                 205

Phe Gly Gln Gly Leu Gly Thr Ile Gly Leu Pro Gly Asp Tyr Thr Pro
                    210                 215                 220

Pro Ser Arg Phe Val Arg Ala Val Tyr Leu Lys Glu His Leu Glu Pro
    225                 230                 235                 240

Ala Ala Asp Glu Thr Lys Gly Val Thr Ala Ala Phe Gln Leu Leu Ala
                    245                 250                 255

Asn Met Thr Val Pro Lys Gly Ala Val Ile Thr Glu Lys Asp Glu Ile
                    260                 265                 270

His Tyr Thr Gln Tyr Thr Ser Val Met Cys Asn Asp Thr Gly Asn Tyr
                    275                 280                 285

Tyr Phe His Leu Tyr Asp Asn Arg Gln Ile Gln Lys Val Asn Leu Phe
                    290                 295                 300

His Glu Asp Leu Asp Arg Leu Glu Pro Lys Val Phe Ser Ala Lys Ala
    305                 310                 315                 320

Glu Glu Ser Ile His Glu Leu Asn
                    325

<210> SEQ ID NO 9
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 9

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
                20                  25                  30

Tyr Pro Arg Arg Tyr Asn Trp Met Ser Glu Ala Asp Gly Arg Ala His
                35                  40                  45

Gln Thr Gln Tyr Ala Phe Ile Gly Met Gly Arg Lys Leu Gly Asn Ile
        50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175
```

```
Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
            195                 200                 205

Phe Gly Gln Gly Leu Gly Thr Ile Gly Leu Pro Gly Asp Tyr Thr Pro
        210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
                275                 280                 285

Tyr Phe His Leu Tyr Asp Asn Arg Gln Ile Gln Lys Val Asn Leu Phe
            290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 10
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 10

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Ala Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205
```

```
Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 11
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 11

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
                20                  25                  30

Tyr Pro Arg Arg Tyr Asn Trp Met Ser Glu Ala Asp Gly Lys Ala His
            35                  40                  45

Gln Thr Gln Tyr Ala Phe Ile Gly Met Gly Arg Lys Leu Gly Asn Ile
        50                  55                  60

Leu Phe Ala Asp Gly Phe Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
        130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
```

```
                225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
                275                 280                 285

Tyr Phe His Leu Tyr Asp Asn Arg Gln Ile Gly Lys Val Asn Leu Phe
                290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 12
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 12

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
                20                  25                  30

Tyr Pro Arg Arg Tyr Asn Trp Met Ser Glu Ala Asp Gly Lys Ala His
                35                  40                  45

Gln Thr Gln Tyr Ala Phe Ile Gly Met Gly Arg Lys Leu Gly Asn Ile
                50                  55                  60

Leu Phe Ala Asp Gly Ile Asn Glu Ser Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
                115                 120                 125

Glu Lys Lys Leu Asp Leu Leu Asp Thr Val Leu Pro Leu His Trp Ile
                130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
                195                 200                 205

Phe Gly Gln Gly Leu Gly Thr Ile Gly Leu Pro Gly Asp Tyr Thr Pro
                210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255
```

```
Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
            325

<210> SEQ ID NO 13
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 13

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Met Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285
```

```
Tyr Phe His Leu Tyr Asp Asn Arg Gln Ile Gln Lys Val Asn Leu Phe
            290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 14
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 14

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Arg Glu Ala Thr
            85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
            130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
            195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
            245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
            290                 295                 300

His Glu Asp Leu Asp Arg Leu Glu Pro Lys Val Phe Ser Ala Lys Ala
```

<210> SEQ ID NO 15
<211> LENGTH: 328
<212> TYPE: PRT
<213> ORGANISM: Artificial Sequence
<220> FEATURE:
<223> OTHER INFORMATION: protein capable of producing the characteristic malodour of human sweat

<400> SEQUENCE: 15

```
Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Asp Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325
```

```
<210> SEQ ID NO 16
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 16

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Val Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 17
<211> LENGTH: 328
<212> TYPE: PRT
<213> ORGANISM: Artificial Sequence
```

<220> FEATURE:
<223> OTHER INFORMATION: protein capable of producing the characteristic malodour of human sweat

<400> SEQUENCE: 17

```
Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Val Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325
```

<210> SEQ ID NO 18
<211> LENGTH: 328
<212> TYPE: PRT
<213> ORGANISM: Artificial Sequence
<220> FEATURE:
<223> OTHER INFORMATION: protein capable of producing the characteristic malodour of human sweat

<400> SEQUENCE: 18

```
Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Val Cys
                100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
            195                 200                 205

Phe Gly Gln Gly Leu Gly Thr Ile Gly Leu Pro Gly Asp Tyr Thr Pro
210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
        290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325
```

<210> SEQ ID NO 19
<211> LENGTH: 328
<212> TYPE: PRT
<213> ORGANISM: Artificial Sequence
<220> FEATURE:
<223> OTHER INFORMATION: protein capable of producing the characteristic malodour of human sweat

<400> SEQUENCE: 19

```
Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
```

20                  25                  30

Tyr Pro Arg Arg Tyr Asn Trp Met Ser Glu Ala Asp Gly Lys Ala His
            35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Gln Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 20
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 20

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

-continued

```
Gln Thr Gln Tyr Ala Phe Ile Gly Met Gly Arg Lys Leu Gly Asn Ile
         50                  55                  60

Leu Phe Ala Asp Gly Ile Asn Glu Asn Gly Leu Ser Cys Ala Ala Leu
 65                  70                  75                  80

Tyr Phe Pro Gly Tyr Ala Glu Tyr Lys Thr Ile Gln Glu Ala Thr
                 85                  90                  95

Val His Ile Ala Pro His Glu Phe Val Thr Trp Ala Leu Ser Ser Cys
            100                 105                 110

Lys Ser Leu Glu Asp Val Lys Glu Lys Ile Arg Ser Leu Thr Ile Val
            115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
            195                 200                 205

Phe Gly Gln Gly Leu Gly Thr Ile Gly Leu Pro Gly Asp Tyr Thr Pro
210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
            290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 21
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 21

Met Cys Thr Ser Leu Thr Leu Glu Thr Ala Asp Arg Asn His Leu Leu
 1               5                  10                  15

Ala Arg Thr Met Asp Phe Ala Phe Gln Leu Gly Thr Glu Val Ile Leu
                 20                  25                  30

Tyr Pro Arg Arg Tyr Asn Trp Met Ser Glu Ala Asp Gly Lys Ala His
             35                  40                  45

Gln Thr Gln Tyr Ala Phe Ile Gly Met Gly Arg Lys Leu Gly Asn Ile
         50                  55                  60

Leu Phe Ala Asp Gly Ile Asn Glu Asn Gly Leu Ser Cys Ala Ala Leu
 65                  70                  75                  80
```

-continued

```
Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
130                 135                 140

Leu Ser Asp Arg Thr Gly Arg Asn Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325
```

<210> SEQ ID NO 22
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 22

```
Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
```

```
                100             105             110
Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
        130                 135             140

Leu Ser Asp Arg Thr Gly Arg Ser Leu Thr Ile Glu Pro Arg Ala Asp
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
            195                 200                 205

Phe Gly Gln Gly Leu Gly Thr Ile Gly Leu Pro Gly Asp Tyr Thr Pro
        210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
        290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 23
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 23

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125
```

```
Glu Lys Lys Leu Asp Leu Leu Asp Thr Val Leu Pro Leu His Trp Ile
    130                 135                 140
Leu Ser Asp Arg Thr Gly Arg Ser Leu Thr Ile Glu Pro Arg Ala Glu
145                 150                 155                 160
Gly Leu Lys Val Tyr Asp Asn Gln Pro Gly Val Met Thr Asn Ser Pro
                165                 170                 175
Asp Phe Ile Trp His Val Thr Asn Leu Gln Gln Tyr Thr Gly Ile Arg
                180                 185                 190
Pro Lys Gln Leu Glu Ser Lys Glu Met Gly Gly Leu Ala Leu Ser Ala
            195                 200                 205
Phe Gly Gln Gly Leu Gly Thr Val Gly Leu Pro Gly Asp Tyr Thr Pro
    210                 215                 220
Pro Ser Arg Phe Val Arg Ala Val Tyr Leu Lys Glu His Leu Glu Pro
225                 230                 235                 240
Ala Ala Asp Glu Thr Lys Gly Val Thr Ala Ala Phe Gln Leu Leu Ala
                245                 250                 255
Asn Met Thr Val Pro Lys Gly Ala Val Ile Thr Glu Lys Asp Glu Ile
                260                 265                 270
His Tyr Thr Gln Tyr Thr Ser Val Met Cys Asn Asp Thr Gly Asn Tyr
            275                 280                 285
Tyr Phe His Leu Tyr Asp Asn Arg Gln Ile Gln Lys Val Asn Leu Phe
    290                 295                 300
His Glu Asp Leu Asp Arg Leu Glu Pro Lys Val Phe Ser Ala Lys Ala
305                 310                 315                 320
Glu Glu Ser Ile His Glu Leu Asn
                325

<210> SEQ ID NO 24
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 24

Met Cys Thr Ser Leu Thr Leu Glu Thr Ala Asp Arg Asn His Leu Leu
1               5                   10                  15
Ala Arg Thr Met Asp Phe Ala Phe Gln Leu Gly Thr Glu Val Ile Leu
                20                  25                  30
Tyr Pro Arg Arg Tyr Asn Trp Met Ser Glu Ala Asp Gly Lys Ala His
            35                  40                  45
Gln Thr Gln Tyr Ala Phe Ile Gly Met Gly Arg Lys Leu Gly Asn Ile
        50                  55                  60
Leu Phe Ala Asp Gly Ile Asn Glu Asn Gly Leu Ser Cys Ala Ala Leu
65                  70                  75                  80
Tyr Phe Pro Gly Tyr Ala Glu Tyr Glu Lys Thr Ile Gln Glu Ala Thr
                85                  90                  95
Val His Ile Ala Pro His Glu Phe Val Thr Trp Ala Leu Ser Ser Cys
                100                 105                 110
Lys Ser Leu Glu Asp Val Lys Glu Lys Met Arg Ser Leu Thr Ile Val
            115                 120                 125
Glu Lys Lys Leu Asp Leu Leu Asp Thr Val Leu Pro Leu His Trp Ile
    130                 135                 140
Leu Ser Asp Arg Thr Gly Arg Ser Leu Thr Ile Glu Pro Arg Ala Glu
145                 150                 155                 160
```

-continued

Gly Leu Lys Val Tyr Asp Asn Gln Pro Gly Val Met Thr Asn Ser Pro
            165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
            195                 200                 205

Phe Gly Gln Gly Leu Gly Thr Ile Gly Leu Ser Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 25
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 25

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
            35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
            165                 170                 175

Asp Phe Ile Trp His Val Thr Asn Leu Gln Gln Tyr Thr Gly Ile Arg

```
            180                 185                 190
Pro Lys Gln Leu Glu Ser Lys Glu Met Gly Gly Leu Ala Leu Ser Ala
            195                 200                 205

Phe Gly Gln Gly Leu Gly Thr Ile Gly Leu Pro Gly Asp Tyr Thr Pro
            210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Ile Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
            290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 26
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 26

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205
```

```
Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Ile Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
            275                 280                 285

Tyr Phe His Leu Tyr Asp Asn Arg Gln Ile Gln Lys Val Asn Leu Phe
        290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 27
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 27

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
                20                  25                  30

Tyr Pro Arg Arg Tyr Asn Trp Met Ser Glu Ala Asp Gly Lys Ala His
            35                  40                  45

Gln Thr Gln Tyr Ala Phe Ile Gly Met Gly Arg Lys Leu Gly Asn Ile
        50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240
```

```
Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
                260                 265                 270

His Tyr Thr Gln Tyr Thr Ser Val Met Cys Asn Asp Thr Gly Asn Tyr
                275                 280                 285

Tyr Phe His Leu Tyr Asp Asn Arg Gln Ile Gln Lys Val Asn Leu Phe
                290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 28
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 28

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
                20                  25                  30

Tyr Pro Arg Arg Tyr Asn Trp Met Ser Glu Ala Asp Gly Lys Ala His
                35                  40                  45

Gln Thr Gln Tyr Ala Phe Ile Gly Met Gly Arg Lys Leu Gly Asn Ile
            50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
                100                 105                 110

Lys Ser Leu Glu Asp Val Lys Glu Lys Met Arg Ser Leu Thr Ile Val
                115                 120                 125

Glu Lys Lys Leu Asp Leu Leu Asp Thr Val Leu Pro Leu His Trp Ile
                130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
                180                 185                 190

Pro Lys Gln Leu Glu Ser Lys Glu Met Gly Gly Leu Ala Leu Ser Ala
                195                 200                 205

Phe Gly Gln Gly Leu Gly Thr Ile Gly Leu Pro Gly Asp Tyr Thr Pro
                210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
```

```
                        260                 265                 270
His Tyr Thr Gln Tyr Thr Ser Val Met Cys Asn Glu Thr Gly Asn Tyr
            275                 280                 285

Tyr Phe His Leu Tyr Asp Asn Arg Gln Ile Gln Lys Val Asn Leu Phe
        290                 295                 300

His Glu Asp Leu Asp Arg Leu Glu Pro Lys Val Phe Ser Ala Lys Ala
305                 310                 315                 320

Glu Glu Ser Ile His Glu Leu Asn
                325

<210> SEQ ID NO 29
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 29

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
                85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
        115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
                245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285
```

Tyr Phe His His Tyr Asp Asn Arg Gln Ile Gln Lys Val Asn Leu Phe
            290                 295                 300

His Glu Asp Leu Asp Arg Leu Glu Pro Lys Val Phe Ser Ala Lys Ala
305                 310                 315                 320

Glu Glu Ser Ile His Glu Leu Asn
            325

<210> SEQ ID NO 30
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 30

Met Cys Thr Ser Leu Thr Leu Glu Thr Ala Asp Arg Asn His Leu Leu
1               5                   10                  15

Ala Arg Thr Met Asp Phe Ala Phe Gln Leu Gly Thr Glu Val Ile Leu
            20                  25                  30

Tyr Pro Arg Arg Tyr Asn Trp Met Ser Glu Ala Asp Gly Lys Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Asn Gly Leu Ser Cys Ala Ala Leu
65                  70                  75                  80

Tyr Phe Pro Gly Tyr Ala Glu Tyr Glu Lys Thr Ile Gln Glu Ala Thr
            85                  90                  95

Val His Ile Ala Pro His Glu Phe Val Thr Trp Ala Leu Ser Ser Cys
            100                 105                 110

Lys Ser Leu Glu Asp Val Lys Glu Lys Met Arg Ser Leu Thr Ile Val
            115                 120                 125

Glu Lys Lys Leu Asp Leu Leu Asp Thr Val Leu Pro Leu His Trp Ile
130                 135                 140

Leu Ser Asp Arg Thr Gly Arg Ser Leu Thr Ile Glu Pro Arg Ala Glu
145                 150                 155                 160

Gly Leu Lys Val Tyr Asp Asn Gln Pro Gly Val Met Thr Asn Ser Pro
            165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Leu Leu Ala
            245                 250                 255

Asn Met Thr Val Pro Lys Gly Ala Val Ile Thr Glu Lys Asp Glu Ile
            260                 265                 270

His Tyr Thr Gln Tyr Thr Ser Val Met Cys Asn Asp Thr Gly Asn Tyr
        275                 280                 285

Tyr Phe His Leu Tyr Asp Asn Arg Gln Ile Gln Lys Val Asn Leu Phe
            290                 295                 300

His Glu Asp Leu Asp Cys Leu Glu Pro Lys Val Phe Ser Ala Lys Ala
305                 310                 315                 320

```
Glu Glu Ser Ile His Glu Leu Asn
            325

<210> SEQ ID NO 31
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat

<400> SEQUENCE: 31

Met Cys Thr Ser Leu Thr Leu Glu Thr Ala Asp Arg Asn His Val Leu
1               5                   10                  15

Ala Arg Thr Met Asp Phe Ala Phe Gln Leu Gly Thr Glu Val Ile Leu
            20                  25                  30

Tyr Pro Arg Arg Tyr Ser Trp Met Ser Glu Ala Asp Gly Arg Ala His
        35                  40                  45

Gln Thr Gln Tyr Ala Phe Ile Gly Met Gly Arg Lys Leu Gly Asn Ile
    50                  55                  60

Leu Phe Ala Asp Gly Ile Asn Glu Ser Gly Leu Ser Cys Ala Ala Leu
65                  70                  75                  80

Tyr Phe Pro Gly Tyr Ala Glu Tyr Glu Lys Thr Ile Arg Glu Ala Thr
                85                  90                  95

Val His Ile Ala Pro His Glu Phe Val Thr Trp Ala Leu Ser Ser Cys
            100                 105                 110

Gln Ser Leu Glu Asp Val Lys Glu Lys Ile Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Asn Leu Thr Ile Glu Pro Arg Ala Asp
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Ile Gly Leu Pro Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Ile Leu Ala
                245                 250                 255

Asn Met Thr Ile Pro Lys Gly Ala Val Ile Thr Glu Glu Asp Glu Ile
            260                 265                 270

His Tyr Thr Gln Tyr Thr Ser Val Met Cys Asn Glu Thr Gly Asn Tyr
        275                 280                 285

Tyr Phe His Leu Tyr Asp Asn Arg Gln Ile Gln Lys Val Asn Leu Phe
    290                 295                 300

His Glu Asp Leu Asp Arg Leu Glu Pro Lys Val Phe Ser Ala Lys Ala
305                 310                 315                 320

Glu Glu Ser Ile His Glu Leu Asn
            325
```

<210> SEQ ID NO 32
<211> LENGTH: 984
<212> TYPE: DNA
<213> ORGANISM: Artificial Sequence
<220> FEATURE:
<223> OTHER INFORMATION: DNA encoding a protein capable of producing the characteristic malodour of human sweat

<400> SEQUENCE: 32

| | | | | | |
|---|---|---|---|---|---|
| atgtgcacat | ctcttacact | tgaaacagct | gatcgtaacc | atcttcttgc | tcgtacaatg | 60 |
| gatttcgctt | tccaacttgg | cacagaagtt | atcctttacc | ctcgtcgtta | caactggatg | 120 |
| tctgaagctg | atggcaaagc | tcatcaaaca | caatacgctt | tcatcggcat | gggccgtaaa | 180 |
| cttggcaaca | tccttttcgc | tgatggcatc | aacgaaaacg | gcctttcttg | cgctgctctt | 240 |
| tacttccctg | gctacgctga | atacgaaaaa | acaatccaag | aagctacagt | tcatatcgct | 300 |
| cctcatgaat | tcgttacatg | ggctctttct | tcttgcaaat | ctcttgaaga | tgttaaagaa | 360 |
| aaaatgcgtt | ctcttacaat | cgttgaaaaa | aaacttgatc | ttcttgatac | agttcttcct | 420 |
| cttcattgga | tcctttctga | tcgtacaggc | cgttctctta | caatcgaacc | tcgtgctgaa | 480 |
| ggccttaaag | tttacgataa | ccaacctggc | gttatgacaa | actctcctga | tttcatctgg | 540 |
| catgttacaa | accttcaaca | atacacaggc | atccgtccta | acaacttga | atctaaagaa | 600 |
| atgggcggcc | ttgctctttc | tgctttcggc | caaggccttg | gcacaatcgg | ccttcctggc | 660 |
| gattacacac | ctccttctcg | tttcgttcgt | gctgtttacc | ttaaagaaca | tcttgaacct | 720 |
| gctgctgatg | aaacaaaagg | cgttacagct | gctttccaac | ttcttgctaa | catgacagtt | 780 |
| cctaaaggcg | ctgttatcac | agaaaaagat | gaaatccatt | acacacaata | cacatctgtt | 840 |
| atgtgcaacg | atacaggcaa | ctactacttc | catctttacg | ataaccgtca | aatccaaaaa | 900 |
| gttaaccttt | tccatgaaga | tcttgatcgt | cttgaaccta | agttttctc | tgctaaagct | 960 |
| gaagaatcta | tccatgaact | taac | | | | 984 |

<210> SEQ ID NO 33
<211> LENGTH: 984
<212> TYPE: DNA
<213> ORGANISM: Artificial Sequence
<220> FEATURE:
<223> OTHER INFORMATION: DNA encoding a protein capable of producing the characteristic malodour of human sweat

<400> SEQUENCE: 33

| | | | | | |
|---|---|---|---|---|---|
| atgtgcacct | ctctgaccct | ggaaaccgct | gaccgtaacc | acctgctggc | tcgtaccatg | 60 |
| gacttcgctt | tccagctggg | taccgaagtt | atcctgtacc | cgcgtcgtta | caactggatg | 120 |
| tctgaagctg | acggtaaagc | tcaccagacc | cagtacgctt | tcatcggtat | gggtcgtaaa | 180 |
| ctgggtaaca | tcctgttcgc | tgacggtatc | aacgaaaacg | gtctgtcttg | cgctgctctg | 240 |
| tacttcccgg | gttacgctga | atacgaaaaa | accatccagg | aagctaccgt | tcacatcgct | 300 |
| ccgcacgaat | tcgttacctg | gctctgtct | tcttgcaaat | ctctggaaga | cgttaaagaa | 360 |
| aaaatgcgtt | ctctgaccat | cgttgaaaaa | aaactggacc | tgctggacac | cgttctgccg | 420 |
| ctgcactgga | tcctgtctga | ccgtaccggt | cgttctctga | ccatcgaacc | gcgtgctgaa | 480 |
| ggtctgaaag | tttacgacaa | ccagccgggt | gttatgacca | actctcctgga | cttcatctgg | 540 |
| cacgttacca | acctgcagca | gtacaccggt | atccgtccga | acagctgga | atctaaagaa | 600 |
| atgggtggtc | tggctctgtc | tgctttcggt | cagggtctgg | gtaccatcgg | tctgccgggt | 660 |
| gactacaccc | cgccgtctcg | tttcgttcgt | gctgtttacc | tgaaagaaca | cctggaaccg | 720 |

```
gctgctgacg aaaccaaagg tgttaccgct gctttccagc tgctggctaa catgaccgtt    780
ccgaaaggtg ctgttatcac cgaaaaagac gaaatccact acacccagta cacctctgtt    840
atgtgcaacg acaccggtaa ctactacttc cacctgtacg acaaccgtca gatccagaaa    900
gttaacctgt tccacgaaga cctggaccgt ctggaaccga agttttctc tgctaaagct    960 gaagaatcta tccacgaact gaac                                           984
```

```
<210> SEQ ID NO 34
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat
<220> FEATURE:
<221> NAME/KEY: VARIANT
<222> LOCATION: (13)..(13)
<223> OTHER INFORMATION: Xaa equals Lys, Asn, Arg, or Gln
<220> FEATURE:
<221> NAME/KEY: VARIANT
<222> LOCATION: (15)..(15)
<223> OTHER INFORMATION: Xaa equals Leu or Val
<220> FEATURE:
<221> NAME/KEY: VARIANT
<222> LOCATION: (38)..(38)
<223> OTHER INFORMATION: Xaa equals Asn, Ser, Gln, Thr, or Cys
<220> FEATURE:
<221> NAME/KEY: VARIANT
<222> LOCATION: (40)..(40)
<223> OTHER INFORMATION: Xaa equals Met, Asn, or Gln
<220> FEATURE:
<221> NAME/KEY: VARIANT
<222> LOCATION: (46)..(46)
<223> OTHER INFORMATION: Xaa equals Lys, or Arg
<220> FEATURE:
<221> NAME/KEY: VARIANT
<222> LOCATION: (69)..(69)
<223> OTHER INFORMATION: Xaa equals Ala, or Gly
<220> FEATURE:
<221> NAME/KEY: VARIANT
<222> LOCATION: (70)..(70)
<223> OTHER INFORMATION: Xaa equals Phe, Ile, or Leu
<220> FEATURE:
<221> NAME/KEY: VARIANT
<222> LOCATION: (73)..(73)
<223> OTHER INFORMATION: Xaa equals Asn, Ser, Gln, Thr, or Cys
<220> FEATURE:
<221> NAME/KEY: VARIANT
<222> LOCATION: (91)..(91)
<223> OTHER INFORMATION: Xaa equals Met or Thr
<220> FEATURE:
<221> NAME/KEY: VARIANT
<222> LOCATION: (93)..(93)
<223> OTHER INFORMATION: Xaa equals Gln or Arg
<220> FEATURE:
<221> NAME/KEY: VARIANT
<222> LOCATION: (95)..(95)
<223> OTHER INFORMATION: Xaa equals Ala, Asp, or Ser
<220> FEATURE:
<221> NAME/KEY: VARIANT
<222> LOCATION: (100)..(100)
<223> OTHER INFORMATION: Xaa equals Ala or Val
<220> FEATURE:
<221> NAME/KEY: VARIANT
<222> LOCATION: (108)..(108)
<223> OTHER INFORMATION: Xaa equals Ala or Val
<220> FEATURE:
<221> NAME/KEY: VARIANT
<222> LOCATION: (111)..(111)
<223> OTHER INFORMATION: Xaa equals Ser or Val
<220> FEATURE:
<221> NAME/KEY: VARIANT
<222> LOCATION: (113)..(113)
<223> OTHER INFORMATION: Xaa equals Lys or Gln
<220> FEATURE:
```

```
<221> NAME/KEY: VARIANT
<222> LOCATION: (122)..(122)
<223> OTHER INFORMATION: Xaa equals Ile, Met, or Leu
<220> FEATURE:
<221> NAME/KEY: VARIANT
<222> LOCATION: (152)..(152)
<223> OTHER INFORMATION: Xaa equals Asn, Ser, Gln, Thr, or Cys
<220> FEATURE:
<221> NAME/KEY: VARIANT
<222> LOCATION: (160)..(160)
<223> OTHER INFORMATION: Xaa equals Asp or Glu
<220> FEATURE:
<221> NAME/KEY: VARIANT
<222> LOCATION: (254)..(254)
<223> OTHER INFORMATION: Xaa equals Ile, Leu, or Val
<220> FEATURE:
<221> NAME/KEY: VARIANT
<222> LOCATION: (260)..(260)
<223> OTHER INFORMATION: Xaa equals Ile, Val, or Leu
<220> FEATURE:
<221> NAME/KEY: VARIANT
<222> LOCATION: (269)..(269)
<223> OTHER INFORMATION: Xaa equals Glu or Lys
<220> FEATURE:
<221> NAME/KEY: VARIANT
<222> LOCATION: (284)..(284)
<223> OTHER INFORMATION: Xaa equals Asp or Glu
<220> FEATURE:
<221> NAME/KEY: VARIANT
<222> LOCATION: (292)..(292)
<223> OTHER INFORMATION: Xaa equals His or Leu
<220> FEATURE:
<221> NAME/KEY: VARIANT
<222> LOCATION: (310)..(310)
<223> OTHER INFORMATION: Xaa equals Cys, Arg, or Lys

<400> SEQUENCE: 34

Met Cys Thr Ser Leu Thr Leu Glu Thr Ala Asp Arg Xaa His Xaa Leu
1               5                   10                  15

Ala Arg Thr Met Asp Phe Ala Phe Gln Leu Gly Thr Glu Val Ile Leu
            20                  25                  30

Tyr Pro Arg Arg Tyr Xaa Trp Xaa Ser Glu Ala Asp Gly Xaa Ala His
        35                  40                  45

Gln Thr Gln Tyr Ala Phe Ile Gly Met Gly Arg Lys Leu Gly Asn Ile
    50                  55                  60

Leu Phe Ala Asp Xaa Xaa Asn Glu Xaa Gly Leu Ser Cys Ala Ala Leu
65                  70                  75                  80

Tyr Phe Pro Gly Tyr Ala Glu Tyr Glu Lys Xaa Ile Xaa Glu Xaa Thr
                85                  90                  95

Val His Ile Xaa Pro His Glu Phe Val Thr Trp Xaa Leu Ser Xaa Cys
            100                 105                 110

Xaa Ser Leu Glu Asp Val Lys Glu Lys Xaa Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Xaa Leu Thr Ile Glu Pro Arg Ala Xaa
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Val Gly Leu Pro Gly Asp Tyr Thr Pro
    210                 215                 220
```

```
Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Xaa Leu Ala
                245                 250                 255

Asn Met Thr Xaa Pro Lys Gly Ala Val Ile Thr Glu Xaa Asp Glu Ile
            260                 265                 270

His Tyr Thr Gln Tyr Thr Ser Val Met Cys Asn Xaa Thr Gly Asn Tyr
        275                 280                 285

Tyr Phe His Xaa Tyr Asp Asn Arg Gln Ile Gln Lys Val Asn Leu Phe
        290                 295                 300

His Glu Asp Leu Asp Xaa Leu Glu Pro Lys Val Phe Ser Ala Lys Ala
305                 310                 315                 320

Glu Glu Ser Ile His Glu Leu Asn
                325

<210> SEQ ID NO 35
<211> LENGTH: 328
<212> TYPE: PRT
<213> ORGANISM: Artificial Sequence
<220> FEATURE:
<223> OTHER INFORMATION: protein capable of producing the characteristic
      malodour of human sweat
<220> FEATURE:
<221> NAME/KEY: Variant
<222> LOCATION: (13)..(13)
<223> OTHER INFORMATION: Xaa equals Lys or Asn
<220> FEATURE:
<221> NAME/KEY: Variant
<222> LOCATION: (15)..(15)
<223> OTHER INFORMATION: Xaa equals Leu or Val
<220> FEATURE:
<221> NAME/KEY: Variant
<222> LOCATION: (38)..(38)
<223> OTHER INFORMATION: Xaa equals Asn or Ser
<220> FEATURE:
<221> NAME/KEY: Variant
<222> LOCATION: (40)..(40)
<223> OTHER INFORMATION: Xaa equals Met or Asn
<220> FEATURE:
<221> NAME/KEY: Variant
<222> LOCATION: (46)..(46)
<223> OTHER INFORMATION: Xaa equals Lys or Arg
<220> FEATURE:
<221> NAME/KEY: Variant
<222> LOCATION: (69)..(69)
<223> OTHER INFORMATION: Xaa equals Ala or Gly
<220> FEATURE:
<221> NAME/KEY: Variant
<222> LOCATION: (70)..(70)
<223> OTHER INFORMATION: Xaa equals Phe or Ile
<220> FEATURE:
<221> NAME/KEY: Variant
<222> LOCATION: (73)..(73)
<223> OTHER INFORMATION: Xaa equals Asn or Ser
<220> FEATURE:
<221> NAME/KEY: Variant
<222> LOCATION: (91)..(91)
<223> OTHER INFORMATION: Xaa equals Met or Thr
<220> FEATURE:
<221> NAME/KEY: Variant
<222> LOCATION: (93)..(93)
<223> OTHER INFORMATION: Xaa equals Gln or Arg
<220> FEATURE:
<221> NAME/KEY: Variant
<222> LOCATION: (95)..(95)
<223> OTHER INFORMATION: Xaa equals Ala or Asp
<220> FEATURE:
<221> NAME/KEY: Variant
<222> LOCATION: (100)..(100)
<223> OTHER INFORMATION: Xaa equals Ala or Val
<220> FEATURE:
```

-continued

```
<221> NAME/KEY: Variant
<222> LOCATION: (108)..(108)
<223> OTHER INFORMATION: Xaa equals Ala or Val
<220> FEATURE:
<221> NAME/KEY: Variant
<222> LOCATION: (111)..(111)
<223> OTHER INFORMATION: Xaa equals Ser or Val
<220> FEATURE:
<221> NAME/KEY: Variant
<222> LOCATION: (113)..(113)
<223> OTHER INFORMATION: Xaa equals Lys or Gln
<220> FEATURE:
<221> NAME/KEY: Variant
<222> LOCATION: (122)..(122)
<223> OTHER INFORMATION: Xaa equals Ile or Met
<220> FEATURE:
<221> NAME/KEY: Variant
<222> LOCATION: (152)..(152)
<223> OTHER INFORMATION: Xaa equals Asn or Ser
<220> FEATURE:
<221> NAME/KEY: Variant
<222> LOCATION: (160)..(160)
<223> OTHER INFORMATION: Xaa equals Asp or Glu
<220> FEATURE:
<221> NAME/KEY: Variant
<222> LOCATION: (216)..(216)
<223> OTHER INFORMATION: Xaa equals Ile or Val
<220> FEATURE:
<221> NAME/KEY: Variant
<222> LOCATION: (219)..(219)
<223> OTHER INFORMATION: Xaa equals Pro or Ser
<220> FEATURE:
<221> NAME/KEY: Variant
<222> LOCATION: (254)..(254)
<223> OTHER INFORMATION: Xaa equals Ile or Leu
<220> FEATURE:
<221> NAME/KEY: Variant
<222> LOCATION: (260)..(260)
<223> OTHER INFORMATION: Xaa equals Ile or Val
<220> FEATURE:
<221> NAME/KEY: Variant
<222> LOCATION: (269)..(269)
<223> OTHER INFORMATION: Xaa equals Glu or Lys
<220> FEATURE:
<221> NAME/KEY: Variant
<222> LOCATION: (284)..(284)
<223> OTHER INFORMATION: Xaa equals Asp or Glu
<220> FEATURE:
<221> NAME/KEY: Variant
<222> LOCATION: (292)..(292)
<223> OTHER INFORMATION: Xaa equals His or Leu
<220> FEATURE:
<221> NAME/KEY: Variant
<222> LOCATION: (310)..(310)
<223> OTHER INFORMATION: Xaa equals Cys or Arg

<400> SEQUENCE: 35

Met Cys Thr Ser Leu Thr Leu Glu Thr Ala Asp Arg Xaa His Xaa Leu
1               5                   10                  15

Ala Arg Thr Met Asp Phe Ala Phe Gln Leu Gly Thr Glu Val Ile Leu
            20                  25                  30

Tyr Pro Arg Arg Tyr Xaa Trp Xaa Ser Glu Ala Asp Gly Xaa Ala His
        35                  40                  45

Gln Thr Gln Tyr Ala Phe Ile Gly Met Gly Arg Lys Leu Gly Asn Ile
    50                  55                  60

Leu Phe Ala Asp Xaa Xaa Asn Glu Xaa Gly Leu Ser Cys Ala Ala Leu
65                  70                  75                  80

Tyr Phe Pro Gly Tyr Ala Glu Tyr Glu Lys Xaa Ile Xaa Glu Xaa Thr
                85                  90                  95

Val His Ile Xaa Pro His Glu Phe Val Thr Trp Xaa Leu Ser Xaa Cys
            100                 105                 110
```

```
Xaa Ser Leu Glu Asp Val Lys Glu Lys Xaa Arg Ser Leu Thr Ile Val
        115                 120                 125

Glu Lys Lys Leu Asp Leu Leu Asp Thr Val Leu Pro Leu His Trp Ile
    130                 135                 140

Leu Ser Asp Arg Thr Gly Arg Xaa Leu Thr Ile Glu Pro Arg Ala Xaa
145                 150                 155                 160

Gly Leu Lys Val Tyr Asp Asn Gln Pro Gly Val Met Thr Asn Ser Pro
                165                 170                 175

Asp Phe Ile Trp His Val Thr Asn Leu Gln Gln Tyr Thr Gly Ile Arg
            180                 185                 190

Pro Lys Gln Leu Glu Ser Lys Glu Met Gly Gly Leu Ala Leu Ser Ala
        195                 200                 205

Phe Gly Gln Gly Leu Gly Thr Xaa Gly Leu Xaa Gly Asp Tyr Thr Pro
    210                 215                 220

Pro Ser Arg Phe Val Arg Ala Val Tyr Leu Lys Glu His Leu Glu Pro
225                 230                 235                 240

Ala Ala Asp Glu Thr Lys Gly Val Thr Ala Ala Phe Gln Xaa Leu Ala
                245                 250                 255

Asn Met Thr Xaa Pro Lys Gly Ala Val Ile Thr Glu Xaa Asp Glu Ile
            260                 265                 270

His Tyr Thr Gln Tyr Thr Ser Val Met Cys Asn Xaa Thr Gly Asn Tyr
        275                 280                 285

Tyr Phe His Xaa Tyr Asp Asn Arg Gln Ile Gln Lys Val Asn Leu Phe
    290                 295                 300

His Glu Asp Leu Asp Xaa Leu Glu Pro Lys Val Phe Ser Ala Lys Ala
305                 310                 315                 320

Glu Glu Ser Ile His Glu Leu Asn
                325

<210> SEQ ID NO 36
<211> LENGTH: 29
<212> TYPE: DNA
<213> ORGANISM: Artificial Sequence
<220> FEATURE:
<223> OTHER INFORMATION: Primer

<400> SEQUENCE: 36
gggactgatc atatgtgcac aagtcttac                              29

<210> SEQ ID NO 37
<211> LENGTH: 34
<212> TYPE: DNA
<213> ORGANISM: Artificial Sequence
<220> FEATURE:
<223> OTHER INFORMATION: Primer

<400> SEQUENCE: 37
attgaggatc cttaattaag ctcatgaata ctct                        34
```

MALODOUR STANDARDS AND INHIBITORS

CROSS REFERENCE TO RELATED APPLICATIONS

This application is the National Phase entry of PCT/EP2011/073275, filed Dec. 19, 2011, which claims priority to European patent application number EP10195789.2 filed Dec. 17, 2010; and U.S. patent application No. 61/424,114, filed Dec. 17, 2010, which are incorporated herein by reference in their entireties.

FIELD OF THE INVENTION

The invention pertains to the field of reaction systems generating malodour, particularly from constituents of human sweat. Specifically, the invention pertains to proteins for generating malodours, substrates for generating such malodour, inhibitors of such malodor generation and test and screening systems for measuring their malodour inhibition efficacy and finding substances previously not known to inhibit malodour generation. Thus, the invention also pertains to the field of deodorants.

REFERENCE TO THE SEQUENCE LISTING

The Sequence Listing file identified as PF70045 BSE0137-00US Sequence Listing-2 ST25.txt, crated on Aug. 2, 2013, 103 KB, is incorporated by reference in its entirety.

BACKGROUND OF THE INVENTION

It is generally accepted that fresh human sweat is odorless, and that the smell of sweat is generated by microorganism colonizing the human skin and particularly the axilla. The smell thus generated from human sweat is considered characteristic in the sense that upon smelling such scent it is immediately clear that the scent indicates human sweat. The smell is widely and according to the present invention considered to be a malodour and can be very pronounced.

It has thus been tried for ages to inhibit the generation of sweat malodour to reduce the malodour or to mask it. In the context of the present invention, "inhibition" designates all means to prevent the formation of sweat malodour from human sweat, including means for slowing down such malodour generation. "Reduction" refers to means for treating the constituents of sweat malodour to render them less intense, e.g. by binding to and immobilizing on a matrix. "Masking" designates those means and efforts intended to affect the human perception of sweat malodour, e.g. by overwhelming a human nose with other, more intense and less malodorous scents, or otherwise reducing or impairing the ability of the human olfactory system to detect one or more malodorous compounds of sweat malodour.

It is desirable to inhibit the formation of sweat malodour and not only to reduce or mask such malodour. One way frequently tried is the application of antiperspirants to human axilla to prevent the formation of sweat. The reasoning is that when no sweat is formed, no sweat malodour will be generated. However, there are concerns that such influencing of human physiological processes may not be sustainable or lead to undesired side effects. In the context of the present invention "inhibitors" therefore are only those substances which are effective to slow down or prevent the formation of one or more constituent of sweat malodour from human sweat other than any relying predominant by on the suppression of secret formation.

There is thus a general need to find effective inhibitors of sweat malodour generation. The search for such inhibitors is hampered by the fact that little is known about the actual formation of sweat malodour, particularly the physiological processes of microorganisms responsible for malodour generation. Further, there is a lack of standardized procedures to compare efficacy of potential malodour generation inhibitors.

Document EP 1 387 891 (also published as WO 02/092024 A2) discloses an isolated N-alpha-acyl-glutamine-aminoacylase reportedly involved in the transformation of odorless precursor compounds found in sweat into malodorous fatty acids. The document further describes the application of this enzyme in high throughput screening for inhibitors.

A disadvantage of the enzyme disclosed in the aforementioned European patent document and correspondingly also of the test system described therein is that the enzyme requires as a cofactor a zinc ion and is thus easily affected by the presence of chelating agents. However, zinc chelating agents like EDTA are not efficient for inhibiting the generation of human sweat malodour when applied to human sweat in vivo. Thus, the test system requires great care when preparing the reagents used therein, and potential inhibitors identified by the test system have to be reanalysed to rule out that their malodour inhibitory effect as determined by the test system is not merely a result of their interference with zinc ions.

It was therefore a problem of the present invention to provide a test system for reproducing a representative pathway of sweat malodour generation without being dependent upon the presence of zinc ions.

BRIEF SUMMARY OF THE INVENTION

According to the invention, there is thus provided a protein comprising an amino acid sequence having
a) a sequence identity of at least 93%, preferably at least 95%, more preferably of at least 98% and most preferably of 100%, and/or
b) a sequence similarity of at least 97%, preferably at least 98%, more preferably of at least 99% and most preferably of 100%,
to an amino acid sequence according to any of SEQ ID NO:2 to 31, SEQ ID NO:34, or SEQ ID NO:35 wherein the sequence identity and sequence similarity are computed according to the EMBOSS needle algorithm having a Gap Open penalty of 10.0, a Gap Extend penalty of 0.5 and using the Blosum62 matrix.

BRIEF DESCRIPTION OF THE DRAWINGS

FIG. 1 illustrates SEQ ID NO:1.
FIG. 2 illustrates SEQ ID NO:2.
FIG. 3 illustrates SEQ ID NO:34.
FIG. 4 illustrates SEQ ID NO:35.
FIG. 5 illustrates SEQ ID NO:5.
FIG. 6 illustrates SEQ ID NO:6.
FIG. 7 illustrates SEQ ID NO:7.
FIG. 8 illustrates SEQ ID NO:8.
FIG. 9 illustrates SEQ ID NO:9.
FIG. 10 illustrates SEQ ID NO:10.
FIG. 11 illustrates SEQ ID NO:11.
FIG. 12 illustrates SEQ ID NO:12.
FIG. 13 illustrates SEQ ID NO:13.
FIG. 14 illustrates SEQ ID NO:14.
FIG. 15 illustrates SEQ ID NO:15.
FIG. 16 illustrates SEQ ID NO:16.
FIG. 17 illustrates SEQ ID NO:17.

FIG. 18 illustrates SEQ ID NO:18.
FIG. 19 illustrates SEQ ID NO:19.
FIG. 20 illustrates SEQ ID NO:20.
FIG. 21 illustrates SEQ ID NO:21.
FIG. 22 illustrates SEQ ID NO:22.
FIG. 23 illustrates SEQ ID NO:23.
FIG. 24 illustrates SEQ ID NO: 24.
FIG. 25 illustrates SEQ ID NO:25.
FIG. 26 illustrates SEQ ID NO:26.
FIG. 27 illustrates SEQ ID NO:27.
FIG. 28 illustrates SEQ ID NO:28.
FIG. 29 illustrates SEQ ID NO:29.
FIG. 30 illustrates SEQ ID NO:30.
FIG. 31 illustrates SEQ ID NO:31.
FIG. 32 illustrates SEQ ID NO:32.
FIG. 33 illustrates SEQ ID NO:33.

DETAILED DESCRIPTION OF THE INVENTION

Figure 34:
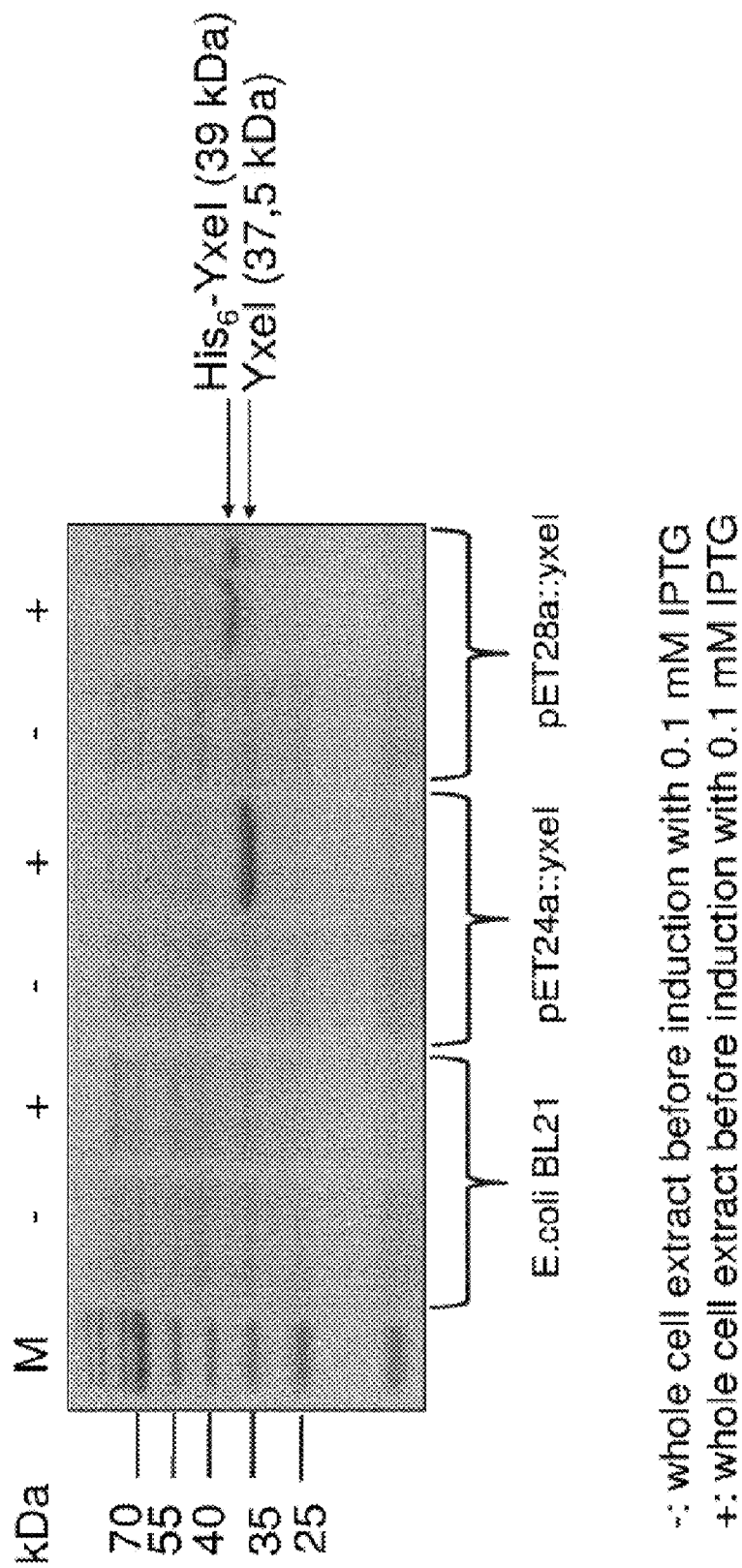
FIG. 34 is an SDS-PAGE analysis showing the results of Example 2.

It has been found that such protein is capable of quickly producing the characteristic malodour of human sweat when brought into contact with fresh, non-malodorous or weakly malodorous human sweat. Significantly, the ability to generate sweat malodour was also found upon contacting of the protein with sterilised human sweat.

Even more important, it has been found that malodour generation from human sweat by this protein does not depend on the presence of zinc ions. The protein also retains its ability to cleave N-alpha-lauroyl-L-glutamine to release a biochemically easy to detect and quantify lauroyl fatty acid even in the presence of concentrations of EDTA sufficient for complexing zinc ions. The protein which is believed to be an enzyme is therefore useful in a malodour standard system and for screening of sweat malodour inhibitors. Even more beneficial, the protein has been found to have a high sequence similarity to proteins found in a huge variety of organisms of different genus, family, order, class and even phylum. The protein of the present invention is thus a representative of a ubiquitous set of proteins of hitherto unknown function occurring in a significant fraction of all microorganisms colonizing the human skin and particularly the axilla. Thus, it is to be expected that inhibitors effective for inhibition of malodour formation by a protein of the present invention will generally be effective to inhibit sweat malodour formation also when applied to human sweat in vivo and to the human skin.

The protein of the present invention preferably is available in isolated form. "Isolated" in the context of the present invention designates that the protein is removed from its original environment and particularly is not contaminated with other microorganism material useful in producing the protein. Even more preferably, the protein is in purified form, which means that the content of the protein in a composition relative to other proteins or peptides having a length of at least 10 amino acids and relative to nucleic acids is at least 80 wt.-%, more particularly at least 90 wt.-%, still more particularly 95 wt.-% and most particularly 99 wt.-% or greater.

The protein, preferably in isolated and even more preferably in purified form, comprises an amino acid sequence having the above sequence identity and/or sequence similarity to an amino acid sequence according to any of SEQ ID NO:2 to 31 (FIG. 2 and FIGS. 5-31), SEQ ID NO:34 (FIG. 3), or SEQ ID NO:35 (FIG. 4). Sequence identity and sequence similarity in the context of the present invention are determined according to the EMBOSS "needle" algorithm. This algorithm is the standard algorithm for pairwise amino acid sequence alignments covering the whole length of both sequences. The algorithm implements the Needleman-Wunsch algorithm (Needleman S. B. and Wunsch C. D., 1970 J. Mol. Biol. 48, 443-453), wherein a penalty for a gap of n positions is computed according to the formula gap opening penalty+(n−1)×gap extension penalty.

The entire length of each amino acid sequence is aligned, and there is no penalty for hanging ends of the overlap.

Gap Open penalty in the context of the present invention is 10.0. The gap extension penalty in the context of the present invention is 0.5. The scoring matrix for comparing amino acid similarities in the context of the present invention is the "Blosum62" matrix. The Gap Open penalty, gap extend penalty and Blosum62 matrix are standard parameters used in the art. Sequence alignments can be performed with these parameters, e.g. via publicly available free tools. For example, the EBI offers a free pairwise sequence alignment service with the parameters of the present invention via its assortment of internet tools.

The protein of the present invention, particularly in an isolated or purified form, may consist of any of the amino acid sequences SEQ ID NO:2 to 31, SEQ ID NO:34, or SEQ ID NO:35, wherein optionally the N-terminal methionine is missing. Proteins having these amino acid sequences without any further added amino acids or modifications are particularly capable of generating the intense and typical malodour when brought into contact with odorless sterilised human sweat. In the context of the present invention, sterilised means that the sweat is filtered by sterile filtration, as known to persons skilled in the art, in particular having a filtration cutoff of 0.4 μm.

The protein of the present invention, preferably in isolated or purified form, preferably comprises or consists of an amino acid sequence according to SEQ ID NO:3, even more preferably according to SEQ ID NO:4. These proteins have been found to be particularly useful for generating a strong and typical malodour of human sweat when brought into contact with sterilised, odorless fresh human sweat. According to the present invention the intensity and flavour of generated sweat malodour is classified by an expert panel of 10 trained odor experts, intensity and flavour being ranked on a scale of 0 (not detectable) to 9 (very intense/very typical). Such assessment is common in the art of odor analysis.

It has particularly been found that proteins comprising isoleucine at position 216 and proline at position 219 of SEQ ID NO:3, e.g. proteins of SEQ ID NO:4, can be easily produced biotechnologically and are capable of producing strong and typical sweat malodour when brought into contact with sterilised fresh human sweat. It is thus preferred that the protein of the present invention comprises or consists of an amino acid sequence according to SEQ ID NO:2 or of a sequence according to any of SEQ ID NO:5 to 31.

Among these, a protein of the present invention is particularly preferred comprising or consisting of the amino acid sequence SEQ ID NO:2. This protein has been isolated from a strain of *Bacillus subtilis* and was particularly found to quickly produce a strong and typical malodour when brought into contact fresh sterilised human sweat, such sweat, as indicated previously, being essentially odorless in its fresh and sterilised state.

The protein of the present invention, particularly the isolated or purified protein comprising or consisting of an amino acid sequence according to any of SEQ ID NO:2 to 31, SEQ ID NO:34, or SEQ ID NO:35, preferably does not cleave 3-methyl-2-hexenic acid-amide and 3-methyl-2-hydroxyhexanoic acid-amide but does cleave N-alpha-lauroyl-L-glutamine. As said before, the cleavage of N-alpha-lauroyl-L-glutamine by the protein is independent of the presence of zinc ions.

According to the invention, there is further provided an isolated nucleic acid coding for a protein of the present invention i.e. a protein having a) a sequence identity of at least 93%, preferably at least 95%, more preferably of at least 98%, and/or b) a sequence similarity of at least 97%, preferably at least 98%, more preferably of at least 99%, to an amino acid sequence according to any of SEQ ID NO:231, SEQ ID NO:34, or SEQ ID NO:35 as defined above. The nucleic acid preferably comprises or consists of a base sequence according to SEQ ID NO:32 (FIG. 32) or SEQ ID:NO 33 (FIG. 33). The nucleotide sequence according to SEQ ID NO:32 is particularly adapted to produce the protein of SEQ ID NO:2 in *Bacillus subtilis*; the nucleic acid comprising the base sequence according to SEQ ID NO:33 is particularly adapted to produce the protein of SEQ ID NO:2 in *E. coli* K12. The skilled person understands that the invention also comprises nucleic acids coding for the protein consisting of SEQ ID NO:2 optimised for expression by other microorganisms than *Bacillus subtilis* and *E. coli* K12, wherein such optimisation is according to the respective codon preference of the microorganism for each respective amino acid.

The nucleic acid of the present invention therefore allows to produce a protein of the present invention biotechnologically, to facilitate the providing of such protein reproducibly and in sufficient quantities.

For this purpose, the invention also provides an expression vector, comprising a nucleic acid according to the invention operably linked to a promoter. And, the invention also provides a host cell, preferably an *E. coli* cell or a *Bacillus subtilis* cell, comprising a nucleic acid coding for a protein according to the present invention, wherein the host cell preferably is transformed with an expression vector of the present invention. The expression vector in the host cell may be separate to or—preferably stably—inserted into the genome of the host cell.

Such biotechnological protein production by recombinant gene expression also offers the possibility of adding N-terminal and/or C-terminal tags to the protein. Such tags comprise tags as e.g. His-tags or Strep-tags or other tags and are well known to the skilled persons. A particular advantage of such tags is easy purification of the respective protein using specific affinity chromatography systems. These purification protocols are well known to skilled persons. Purification of proteins with His-tags on resins functionalized with Ni-NTA or Ni-IDA is of particular advantage, as such resins are easily available (e.g. from GE Healthcare, Uppsala, Sweden). Another advantage of His-tags attached to proteins of this invention is the non-interference of the His-tag with the enzymatic activity of the enzyme and its use according to this invention. So, such a purification tag might be used to assist protein purification, in case it would be beneficial.

Figure 35:
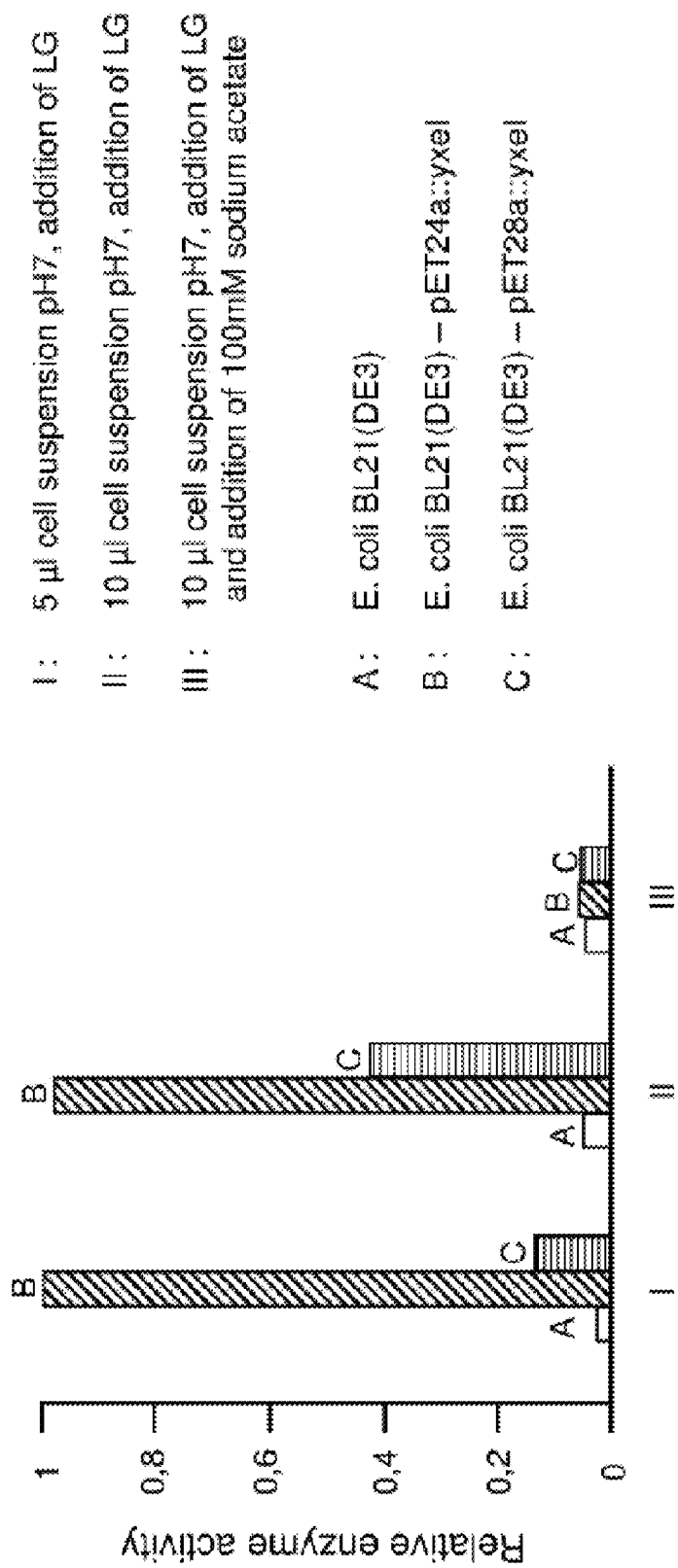
FIG. 35 is a bar graph showing the enzyme activity results obtained in Example 3.

On the other hand, it is known to the skilled person that such tags might interfere with protein production efficiency and/or specific enzyme activity. As seen in FIG. 35, this happened here as well: total enzyme activity in the cell culture for the His-tagged protein is lower than for the protein without His-tag.

This offers a particular advantageous possibility of either producing larger amounts of protein for larger demands, as for large numbers of tests (e.g. for screening of large numbers of potential inhibitors) or the production of purified protein for detailed biochemical tests (as e.g. determination of enzyme kinetics, inhibitor binding constants etc.)

In view of the above problem of the present invention, there is also provided a malodour standard composition. The malodour standard composition of the present invention comprises a protein of the present invention, preferably an isolated or purified protein, further preferably comprising or consisting of an amino acid sequence according to any of SEQ ID NO:2 to 31, SEQ ID NO:34, or SEQ ID NO:35, together with a substance cleavable by the protein to generate a malodorous product. The cleavable substance may be an ingredient of natural, fresh and sterilized human sweat. According to the present invention, malodour standard compositions are particularly preferred wherein the cleavable substance is N-alpha-lauroyl-L-glutamine.

The malodour standard compositions of the present invention are particularly useful for generating a strong and typical malodour of human sweat when being brought into contact with fresh and, prior to said contact, essentially odorless human sweat. A particular advantage of such malodour standard compositions according to the present invention is that they are not dependent upon the presence of zinc ions in the malodour standard composition or in sweat. The malodour standard compositions of the present invention thus allow to study and influence the generation of a very typical malodour of human sweat under reproducible conditions, substantially eliminating factors like varying skin surface or sweat temperatures of test persons.

The malodour standard compositions according to the present invention are particularly suitable for finding and testing the efficacy of substances influencing the generation, the intensity and the "flavour" of sweat malodour. This can be achieved by adding a candidate substance for modifying the speed, intensity or "flavour" of sweat malodour to a malodour standard composition of the present invention which is then brought into contact with human sweat, particularly with fresh and preferably sterilised human sweat. Also, the candidate substance can be added to sweat, particularly fresh and preferably sterilised sweat which is then brought into contact with a malodour standard composition of the present invention.

The malodour standard composition according to the present invention is not limited to the above described malodour standard compositions. The malodour standard composition can also comprise an isolated protein comprising an amino acid sequence having a) a sequence identity of at least 93%, preferably at least 95%, more preferably of at least 98% and/or b) a sequence similarity of at least 97%, preferably at least 98%, more preferably of at least 99%, to an amino acid sequence according to SEQ ID NO:1, wherein sequence identity and sequence similarity are computed according to the EMBOSS needle algorithm having a Gap Open penalty of 10.0, a Gap Extent penalty of 0.5 and using the Blosum62 matrix. The amino acid sequence SEQ ID NO:1 is known from *Bacillus subtilis*. However, it was not known that such protein, when brought into contact with odourless human sweat, is capable of producing a typical and intense sweat malodour. The protein is thus also useful in malodour standard compositions of the present invention.

The malodour standard composition of the present invention preferably comprises a protein comprising or consisting of an amino acid sequence according to any of SEQ ID NO:1 to 31, SEQ ID NO:34, OR SEQ ID NO:35, preferably comprising or consisting of an amino acid sequence according to SEQ ID NO:2 or any of SEQ ID NO:5 to 31, SEQ ID NO:34, OR SEQ ID NO:35. Particularly preferred are such malodour standard compositions wherein the protein for generating sweat malodour consists of a purified protein consisting of any of amino acid sequences SEQ ID NO:1 to 31, SEQ ID NO:34, or SEQ ID NO:35, particularly preferably SEQ ID NO:2 or 5 to 31, and most preferably of SEQ ID NO:2.

Thus, according to the present invention there is provided a malodour standard composition consisting of
- an isolated or purified protein consisting any of the amino acid sequences SEQ ID NO:1, SEQ ID NO:2 to 31, SEQ ID NO:34, or SEQ ID NO:35
- N-alpha-lauroyl-L-glutamine
- and a carrier.

The carrier preferably is a liquid carrier and most preferably is a water buffer adjusted to a pH of >4, even more preferably of 5 to 9 and most preferably of 6.2 to 7.8. It is particularly preferred that such buffer is a buffer made of water, 50 mM $NaH_2PO_4/K_2HPO_4$ and 50 mM NaCl. Such carrier is easy to produce reproducibly and insufficient quantities.

According to the invention, there is also provided a malodour inhibition composition. The malodour inhibition composition comprises a malodour standard composition according to the present invention and a potential inhibitor of the cleavage reaction to generate a malodorous product such malodour inhibition composition of the present invention allows to test easily and reproducibly in a standardized way the efficacy of a potential sweat malodour in inhibitor.

According to the invention, the malodour inhibition composition therefore comprises
- a preferably isolated or purified protein comprising or consisting of an amino acid sequence according to any of SEQ ID NO:1, SEQ ID NO:2 to 31, SEQ ID NO:34, or SEQ ID NO:35,
- N-alpha-lauroyl-L-glutamine and
- a carrier for allowing the cleavage of N-alpha-L-lauroyl-L-glutamine by the protein in the absence of an inhibitor, and
- the candidate inhibitor.

Even more preferably, the malodour inhibitor composition of the present invention consists of
- an isolated or purified protein consisting of the amino acid sequence according to any of SEQ ID NO:1, SEQ ID NO:2, or SEQ ID NO:5 to 31,
- N-alpha-lauroyl-L-glutamine,
- a carrier for allowing the cleavage of N-alpha-L-lauroyl-L-glutamine by the protein in the absence of an inhibitor, and
- a candidate inhibitor.

In the malodour inhibition composition of the present invention, the carrier preferably is a solution, in water, of 50 mM NaCl and 50 mM $NaH_2PO_4/K_2HPO_4$ at pH 7.

The present invention further provides a malodour inhibitor screening system, comprising a—preferably isolated—protein comprising an amino acid sequence having
a) a sequence identity of at least 93%, preferably at least 95%, more preferably of at least 98%, and/or
b) a sequence similarity of at least 97%, preferably at least 98%, more preferably of at least 99%,
to an amino acid sequence according to any of SEQ ID NO:1 to 31, SEQ ID NO:34, or SEQ ID NO:35, wherein the sequence identity and sequence similarity are computed according to the EMBOSS needle algorithm having a Gap Open penalty of 10.0, a Gap Extend penalty of 0.5 and using the Blosum62 matrix,
together with a substance cleavable by the protein to generate a malodorous product under conditions allowing such cleavage, and
a set of inhibitor candidate substances to be screened.

The malodour inhibitor screening system thus preferably comprises a machine performing the steps of reacting the protein and the cleavable substance in the presence of a selected inhibitor candidate substance under conditions which, in the absence of an effective inhibitor, allow the cleavage of the cleavable substance to generate a malodorous product.

Again, the cleavable substance preferably is N-alpha-lauroyl-L-glutamine. Also for the benefits discussed above the protein preferably is an isolated or purified protein.

Particularly preferred is a malodour inhibitor screening system of the present invention, wherein the protein is an isolated or purified protein consisting of an amino acid sequence according to any of SEQ ID NO:1, 2 to 31, SEQ ID NO:34, or SEQ ID NO:35 and most preferably is a purified protein consisting of an amino acid sequence according to SEQ ID NO:2.

The conditions allowing such cleavage include preferably the presence of a water buffer comprising 50 mM NaCl and 50 mM $NaH_2PO_4/K_2HPO_4$ at pH 7.

In summary, a malodour inhibitor screening system is particularly preferred which comprises
- a purified protein consisting of the amino acid sequence according to any of SEQ ID NO:1, SEQ ID NO:2, or SEQ ID NO:3 to 31, SEQ ID NO:34, or SEQ ID NO:35,
- N-alpha-lauroyl-L-glutamine,
- a water buffer of 50 mM NaCl and 50 mM $NaH_2PO_4/K_2HPO_4$ at pH 7,
- an array of inhibitor candidate substances, and
- an automat for mixing the protein, N-alpha-lauroyl-L-glutamine and one or more inhibitor candidate substances into the buffer.

Such malodour inhibitor screening system is particularly adapted to be used in high throughput screening applications for testing the efficacy of a large assortment of potential inhibitor substances in varying concentrations. The malodour inhibitor screening system of the present invention thus advantageously aids in the identification of further useful sweat malodour inhibitors. The system further realizes the advantages involved with the protein and malodour standard composition of the present invention, particularly that themalodour generation is independent of zinc ions.

Again, the formation of malodour and the inhibition of malodour formation can be analysed and quantified by an expert panel as indicated above. Also preferred and particularly useful in high throughput applications, however, is a system according to the present invention wherein the substance to be cleaved and/or a product of such cleavage reaction is detected automatically, e.g. by gas chromatography or optically via photometry, fluorescence photometry or luminescence-photometry upon addition of further reactants. Such means for detection are known to the skilled person, e.g. from example 8 of EP 1387891 B1.

Accordingly, the present invention also provides for a standardizable method of generating a malodour, comprising the step of reacting a protein comprising or consisting of an amino acid sequence having
a) a sequence identity of at least 93%, preferably at least 95%, more preferably of at least 98%, and/or
b) a sequence similarity of at least 97%, preferably at least 98%, more preferably of at least 99%,
to an amino acid sequence according to any of SEQ ID NO:1 to 31, SEQ ID NO:34, or SEQ ID NO:35, wherein the sequence identity and sequence similarity are computed according to the EMBOSS needle algorithm having a Gap Open penalty of 10.0, a Gap Extend penalty of 0.5 and using the Blosum62 matrix, with a substance cleavable by this protein under conditions allowing such cleavage to produce a malodour, wherein the substance preferably is N-alpha-lauroyl-L-glutamine.

The method is preferably performed in fresh and sterilised human sweat, or in a water buffer of 50 mM NaCl and 50 mM $NaH_2PO_4/K_2HPO_4$ buffer at pH 7.

The protein preferably consists of an amino acid sequence according to any of SEQ ID NO:1 to 31, SEQ ID NO:34, or SEQ ID NO:35, preferably according to any of SEQ ID NO:1, SEQ ID NO:2, or SEQ ID NO:5 to 31 and most preferably according to SEQ ID NO:2.

Further, the invention provides a method of screening for malodour inhibitors the method comprises the steps of 1. incubating a protein comprising an amino acid sequence having
   a) a sequence identity of at least 93%, preferably at least 95%, more preferably of at least 98%, and/or
   b) a sequence similarity of at least 97%, preferably at least 98%, more preferably of at least 99%,
   to an amino acid sequence according to any of SEQ ID NO:1 to 31, SEQ ID NO:34, or SEQ ID NO: 35, wherein the sequence identity and sequence similarity are computed according to the EMBOSS needle algorithm having a Gap Open penalty of 10.0, a Gap Extend penalty of 0.5 and using the Blosum62 matrix,
   together with a substance cleavable by the protein under conditions allowing for such cleavage reaction in the absence of in inhibitor and
   an inhibitor candidate substance for potentially inhibiting the cleavage reaction, and
2. measuring malodour generation.

The invention is further described by reference to the examples and figures. These examples are not to be understood to limit the scope of the claims.

EXAMPLES

Example 1

Amplification of the yxel Gene by PCR and Cloning into *E. Coli* Expression Vectors Genomic DNA of a *Bacillus subtilis* strain, isolated from human armpit was used as template for PCR amplification. The primers Forward (5'-GGGACTGATCATATGTGCA-CAAGTCTTAC-3'), (SEQ ID NO:36), and Reverse (5'-AT-TGAGGATCCTTAATTAAGCTCATGAATACTCT-3'), (SEQ ID NO:37), were used for PCR amplification.

The resulting PCR-product was treated with restriction endonucleases NdeI and BamHI (New England Biolabs, Frankfurt, Germany) according to instructions of the manufacturer and cloned into plasmids pET24a (Merck, Darmstadt, Germany) and pET28a (Merck, Darmstadt, Germany). The resulting expression vectors were called pET24a::yxel or pET28a::yxel. They contain a nucleic acid coding for a protein of SEQ ID NO 1. In vector pET28a, the protein is linked to a His-Tag of 6 consecutive histidine amino acids.

Example 2

Gene Expression and Protein Production in *E. Coli*

*E. coli* BL21(DE3) was used as expression host. The strains (either without plasmid or carrying the expression vectors described in Example 1) were grown at 37° C. in 100 ml Luria-Bertani medium using 250 ml shake flasks with vigourous shaking. Plasmid-containing strains were grown in presence of Luria-Bertani medium containing 30 mg/l kanamycin. After the cell density reached an OD600 of 1, IPTG was added to a final concentration of 0.1 mM, followed by additional incubation under identical conditions for another 2 hours.

1.5 ml samples were taken from the cultures, cells were harvested by centrifugation and analyzed by SDS-PAGE followed by Coomasie staining. Strong gene expression and protein production was observed after induction, as shown by FIG. 34.

Example 3

Determination of Enzyme Activity and Test for Inhibitors Effects

Cells obtained as in example 2 were harvested by centrifugation and washed twice with PBS buffer to remove residual medium components. The final cell pellet was resuspended in PBS buffer (per liter water: 8 g NaCl, 0.2 g KCl, 1.44 g $Na_2HPO_4$, 0.24 g K $H_2PO_4$, pH 7.4) to reach a final OD600 of 30. This cell suspension of strains (either without plasmid or carrying the expression vectors described in Example 1) was used for the activity tests. The washed cell suspensions were contacted in PBS buffer with N-alpha-lauryl-glutamin (0.2 mg/ml final concentration, "LG" in FIG. 35), at 37° (final volume 0.25 ml) for 15 min. The actual test was performed as described in example 7 of WO 02/092024 A2, with GC as the test method. The plasmid-free strain showed some background activity, whereas the strains carrying the expression vectors showed strong enzyme activity, as can be seen in FIG. 35. This figure displays the enzyme activity relative to the activity of the enzyme of the present invention expressed in pET 24a. As a side note, contacting this enzyme with fresh human sweat results in development of an intense smell of human sweat.

As a test for inhibition of the activity, sodium acetate was added to one set of samples to a final concentration of 100 mM. As a result, the enzyme activity was inhibited to the level of the background activity of the plasmid-free *E. coli* strain.

The assay was repeated with enzymes having an amino acid sequence according to SEQ ID NO:2, and SEQ ID NO:5 to 31, respectively. All enzymes likewise produced an intense smell of human sweat when brought into contact with fresh, odorless human sweat.

The invention claimed is:

1. A malodour standard composition, comprising
a protein, comprising an amino acid sequence having
 a) a sequence identity of at least 93% and/or
 b) a sequence similarity of at least 97%,
to an amino acid sequence according to any of SEQ ID NO:1 to 31, wherein sequence identity and sequence similarity are computed according the EMBOSS needle algorithm having a Gap Open penalty of 10.0, a Gap Extend penalty of 0.5 and using the Blosum62 matrix,
wherein the protein has N-alpha-lauroyl-L-glutamine cleaving activity;
together with N-alpha-lauroyl-L-glutamine cleavable by the protein to generate a malodorous product.

2. A malodour inhibition composition, comprising the malodour standard composition according to claim 1 and an inhibitor candidate substance to be screened for inhibition of the N-alpha-lauroyl-L-glutamine cleaving activity of the protein to prevent generation of a malodorous product.

3. A method of screening for malodour inhibitors, comprising the steps of 1) incubating
    a protein, comprising an amino acid sequence having
        a) a sequence identity of at least 93 and/or
        b) a sequence similarity of at least 97%,
    to an amino acid sequence according to any of SEQ ID NO:1 to 31, wherein sequence identity and sequence similarity are computed according the EMBOSS needle algorithm having a Gap Open penalty of 10.0, a Gap Extend penalty of 0.5 and using the Blosum62 matrix, wherein the protein has N-alpha-lauroyl-L-glutamine cleaving activity;
    together with N-alpha-lauroyl-L-glutamine, and
    an inhibitor candidate substance,
    under conditions for generation of a malodorous product by cleavage of the N-alpha-lauroyl-L-glutamine; and
2) measuring malodour generation.

4. The method according to claim 3, wherein the protein is an isolated or purified protein consisting of an amino acid sequence according to any of SEQ ID NO:1 to 31.

5. The malodour standard composition according to claim 1 further comprising a pH 5 to 9 water buffer.

6. The malodour standard composition according to claim 5, wherein the water buffer comprises water, 50 mM NaH$_2$PO$_4$/K2HPO4 and 50 mM NaCl.

7. The malodour inhibition composition according to claim 2, further comprising a carrier which allows cleavage of N-alpha-lauroyl-L-glutamine in the absence of an inhibitor of cleavage of the N-alpha-lauroyl-L-glutamine by the protein.

8. The method according to claim 3, further comprising a machine for reacting the protein and the N-alpha-lauroyl-L-glutamine in the presence of the inhibitor candidate substance.

9. The method according to claim 8, which is a high-throughput screening method.

10. The method according to claim 9, wherein the inhibitor candidate substance is an array of inhibitor candidate substances.

11. The method according to claim 8, wherein the machine mixes the protein, the N-alpha-lauroyl-L-glutamine and one or more inhibitor candidate substances with a buffer.

12. A malodour standard composition, comprising
    a protein having an amino acid sequence according to SEQ ID NO:34 or SEQ ID NO:35, wherein the protein has N-alpha-lauroyl-L-glutamine cleaving activity;
    together with N-alpha-lauroyl-L-glutamine cleavable by the protein to generate a malodorous product.

13. A method of screening for malodour inhibitors, comprising:
1) incubating the malodour standard composition of claim 12 with an inhibitor candidate substance under conditions for generation of a malodorous product by cleavage of the N-alpha-lauroyl-L-glutamine; and
2) measuring malodour generation.

* * * * *